(12) United States Patent
Kobayashi et al.

(10) Patent No.: US 12,406,474 B2
(45) Date of Patent: Sep. 2, 2025

(54) RECORDING MEDIUM, METHOD FOR GENERATING LEARNING MODEL, SURGICAL SUPPORT DEVICE AND INFORMATION PROCESSING METHOD

(71) Applicant: Anaut Inc., Tokyo (JP)

(72) Inventors: Nao Kobayashi, Tokyo (JP); Yuta Kumazu, Tokyo (JP); Seigo Senya, Tokyo (JP)

(73) Assignee: Anaut Inc., Tokyo (JP)

( * ) Notice: Subject to any disclaimer, the term of this patent is extended or adjusted under 35 U.S.C. 154(b) by 472 days.

(21) Appl. No.: 18/018,219

(22) PCT Filed: Jul. 29, 2021

(86) PCT No.: PCT/JP2021/028009
§ 371 (c)(1),
(2) Date: Jan. 26, 2023

(87) PCT Pub. No.: WO2022/025151
PCT Pub. Date: Feb. 3, 2022

(65) Prior Publication Data
US 2023/0281968 A1    Sep. 7, 2023

(30) Foreign Application Priority Data
Jul. 30, 2020 (JP) .................. 2020-129614

(51) Int. Cl.
*G06V 10/77* (2022.01)
*A61B 1/00* (2006.01)
(Continued)

(52) U.S. Cl.
CPC ...... *G06V 10/774* (2022.01); *A61B 1/000096* (2022.02); *A61B 1/00045* (2013.01);
(Continued)

(58) Field of Classification Search
CPC .... G06V 10/774; G06V 10/776; G06V 20/50; G06V 2201/034; G06V 10/26;
(Continued)

(56) References Cited

U.S. PATENT DOCUMENTS

2005/0222491 A1    10/2005 Noda et al.
2014/0343586 A1    11/2014 Sakuragi
(Continued)

FOREIGN PATENT DOCUMENTS

CN      108814717 A    11/2018
EP       3528263 A1     8/2019
(Continued)

OTHER PUBLICATIONS

Suzuki et al., "Standard LapaColle and The critical view of safety", Journal of Clinical Surgery, vol. 71, No. 8, Igaku-Shoin LTD., Kanehara, Yu, Aug. 20, 2016, pp. 992-995, ISSN: 0386-9857, particularly, "Introduction" column, "Understanding of anatomy" column in "Surgical procedure" column, "Confirmation of exfoliated layer" column in "Surgical procedure" column.
(Continued)

*Primary Examiner* — Neil R Mclean
(74) *Attorney, Agent, or Firm* — Bret E. Field; Bozicevic, Field & Francis LLP

(57) ABSTRACT

A computer readable non-transitory recording medium storing a computer program causing a computer to execute processing of: acquiring an operation field image obtained by shooting an operation field of an endoscopic surgery; and recognizing a loose connective tissue part included in the surgical field image by inputting the surgical field image acquired to a learning model so trained as to output information related to loose connective tissue when the operation field image is input.

22 Claims, 24 Drawing Sheets

(51) Int. Cl.
- *G06T 7/00* (2017.01)
- *G06V 10/774* (2022.01)
- *G06V 10/776* (2022.01)
- *G06V 20/50* (2022.01)

(52) U.S. Cl.
CPC .......... *G06T 7/0012* (2013.01); *G06V 10/776* (2022.01); *G06V 20/50* (2022.01); *G06T 2207/10024* (2013.01); *G06T 2207/10068* (2013.01); *G06T 2207/20021* (2013.01); *G06T 2207/20081* (2013.01); *G06T 2207/30096* (2013.01); *G06V 2201/034* (2022.01)

(58) Field of Classification Search
CPC ................. G06V 10/454; G06V 10/82; G06V 2201/031; A61B 1/000096; A61B 1/00045; A61B 1/000094; A61B 34/20; G06T 7/0012; G06T 2207/10024; G06T 2207/10068; G06T 2207/20021; G06T 2207/20081; G06T 2207/30096; G06T 7/11; G06T 2207/20084; G06N 20/00
USPC ......................................................... 382/128
See application file for complete search history.

(56) References Cited

U.S. PATENT DOCUMENTS

| | | |
|---|---|---|
| 2018/0181875 A1 | 6/2018 | Motohashi et al. |
| 2018/0360342 A1 | 12/2018 | Fuimaono et al. |
| 2019/0069957 A1 | 3/2019 | Barral et al. |
| 2019/0096060 A1 | 3/2019 | Zhang et al. |
| 2019/0130216 A1 | 5/2019 | Tomioka et al. |
| 2020/0093544 A1 | 3/2020 | Azizian |
| 2020/0097727 A1 | 3/2020 | Stumpe |
| 2020/0193236 A1* | 6/2020 | Oosake ................ G06V 10/454 |
| 2021/0015343 A1 | 1/2021 | Uyama et al. |
| 2021/0287395 A1 | 9/2021 | Ishikake et al. |

FOREIGN PATENT DOCUMENTS

| | | | |
|---|---|---|---|
| JP | 2001-236337 A | 8/2001 | |
| JP | 2005-287839 A | 10/2005 | |
| JP | 2006-325638 A | 12/2006 | |
| JP | 2013-154037 A | 8/2013 | |
| JP | 2014-113311 A | 6/2014 | |
| JP | 2018-067266 A | 4/2018 | |
| JP | 2019-075159 A | 5/2019 | |
| JP | 2019-087229 A | 6/2019 | |
| JP | 2019-162339 A | 9/2019 | |
| JP | 2020-521946 A | 7/2020 | |
| WO | WO2019054045 A1 | 3/2019 | |
| WO | WO-2020110278 A1 * | 6/2020 | ............. G06N 3/084 |
| WO | WO2021152784 A1 | 8/2021 | |
| WO | WO2021153797 A1 | 8/2021 | |

OTHER PUBLICATIONS

English Translation of International Search Report for PCT Application No. PCT/JP2021/028009 mailed Sep. 21, 2021, 3 pages.

Shinohara et al., WS15-2 "Micro anatomical structure recognition by image segmentation; Visualization of loose connective tissue gap in robot-assisted gastric cancer surgery", Abstracts of The 75th General Meeting of the Japanese Society of Gastroenterological Surgery, Japan, Japanese Society of Gastroenterological Surgery, Dec. 2020, p. 134.

\* cited by examiner

FIG. 18

| CONFIDENCE | EVALUATION FACTOR |
|---|---|
| 0~0.1 | 4 |
| 0.1~0.2 | 2 |
| 0.2~0.3 | 0 |
| 0.3~0.4 | -2 |
| 0.4~0.5 | -4 |
| 0.5~0.6 | -4 |
| 0.6~0.7 | -2 |
| 0.7~0.8 | 0 |
| 0.8~0.9 | 2 |
| 0.9~1 | 4 |

FIG. 19A

| CONFIDENCE | PERCENTAGE OF PIXELS | EVALUATION FACTOR | SCORE |
|---|---|---|---|
| 0~0.1 | 80 | 4 | 320 |
| 0.1~0.2 | 0 | 2 | 0 |
| 0.2~0.3 | 0 | 0 | 0 |
| 0.3~0.4 | 0 | -2 | 0 |
| 0.4~0.5 | 0 | -4 | 0 |
| 0.5~0.6 | 0 | -4 | 0 |
| 0.6~0.7 | 0 | -2 | 0 |
| 0.7~0.8 | 0 | 0 | 0 |
| 0.8~0.9 | 0 | 2 | 0 |
| 0.9~1 | 20 | 4 | 80 |
| TOTAL | 100 | — | 400 |

FIG. 19B

| CONFIDENCE | PERCENTAGE OF PIXELS | EVALUATION FACTOR | SCORE |
|---|---|---|---|
| 0~0.1 | 30 | 4 | 120 |
| 0.1~0.2 | 20 | 2 | 40 |
| 0.2~0.3 | 10 | 0 | 0 |
| 0.3~0.4 | 10 | -2 | -20 |
| 0.4~0.5 | 10 | -4 | -40 |
| 0.5~0.6 | 6 | -4 | -24 |
| 0.6~0.7 | 4 | -2 | -8 |
| 0.7~0.8 | 4 | 0 | 0 |
| 0.8~0.9 | 4 | 2 | 8 |
| 0.9~1 | 2 | 4 | 8 |
| TOTAL | 100 | — | 84 |

FIG. 19C

| CONFIDENCE | PERCENTAGE OF PIXELS | EVALUATION FACTOR | SCORE |
|---|---|---|---|
| 0~0.1 | 40 | 4 | 160 |
| 0.1~0.2 | 20 | 2 | 40 |
| 0.2~0.3 | 10 | 0 | 0 |
| 0.3~0.4 | 6 | -2 | -12 |
| 0.4~0.5 | 4 | -4 | -16 |
| 0.5~0.6 | 2 | -4 | -8 |
| 0.6~0.7 | 4 | -2 | -8 |
| 0.7~0.8 | 4 | 0 | 0 |
| 0.8~0.9 | 4 | 2 | 8 |
| 0.9~1 | 6 | 4 | 24 |
| TOTAL | 100 | — | 188 |

RECORDING MEDIUM, METHOD FOR GENERATING LEARNING MODEL, SURGICAL SUPPORT DEVICE AND INFORMATION PROCESSING METHOD

CROSS-REFERENCE TO RELATED APPLICATIONS

This application is the national phase of PCT International Application No. PCT/JP2021/028009 which has an International filing date of Jul. 29, 2021 and designated the United States of America.

FIELD

The invention relates to a recording medium, a method for generating a learning model, a surgical support device and an information processing method.

BACKGROUND

Laparoscopic surgery involves surgery to remove a lesion, such as a malignant tumor or the like formed in the patient's body. The interior of the patient's body is then imaged via a laparoscope and the obtained observation image is then displayed on the monitor (see Japanese Patent Application Laid-Open No. 2005-287839, for example).

The surgeon performs laparoscopic surgery using various surgical tools while viewing the observation images displayed on the monitor. For example, the surgeon uses forceps to expand the tissue containing the lesion in an appropriate direction and exposes the loose connective tissue that is present between the tissue containing the lesion and the tissue to be left. The surgeon resects the exposed loose connective tissue using energy-based surgical tools such as electrocautery to exfoliate the tissue containing the lesion from the tissue to be left.

Due to the presence of blood vessels, nerves, humoral substrates and various cells around the fibers that make up the loose connective tissue, however, finding the loose connective tissue from the surgical field image is not necessarily easy for the surgeon.

The object of the present invention is to provide a recording medium, a method for generating a learning model, a surgical support device, and an information processing method that can output the recognition result of a loose connective tissue part from an operation field image.

A computer readable non-transitory recording medium in one aspect of the present invention is a recording medium storing a computer program causing a computer to execute processings of: acquiring an operation field image obtained by shooting an operation field of endoscopic surgery; and outputting a recognition result of loose connective tissue included in the surgical field image by inputting the surgical field image acquired to a learning model so trained as to output information related to loose connective tissue when the operation field image is input.

A method for generating a learning model in one aspect of the present invention comprises: acquiring training data including an operation field image obtained by shooting an operation field of endoscopic surgery and correct data indicating a loose connective tissue part within the surgical field image; and generating a learning model that outputs a recognition result of loose connective tissue based on sets of training data acquired when the operation field image is input.

A surgical support device in one aspect of the present invention comprises a processor and a storage storing instructions causing the processor to execute processes of: acquiring an operation field image obtained by shooting an operation field of endoscopic surgery; recognizing a loose connective tissue part included in the surgical field image acquired using a learning model so trained as to output a recognition result of loose connective tissue when the operation field image is input; and outputting support information related to the endoscopic surgery based on the recognition result.

An information processing method in one aspect of the present invention comprises: acquiring an operation field image obtained by shooting an operation field of endoscopic surgery; recognizing a loose connective tissue part included in the surgical field image acquired using a learning model so trained as to output a recognition result of loose connective tissue when the operation field image is input; and outputting support information related to the endoscopic surgery based on the recognition result.

According to the present application, the recognition results of the loose connective tissue part can be output from the surgical field image.

The above and further objects and features of the invention will more fully be apparent from the following detailed description with accompanying drawings.

FIG. 18 illustrates one example of an evaluation factor table;

FIGS. 19A-19C illustrate one example of results of calculating scores;

DESCRIPTION OF EMBODIMENTS

The present invention will be described in details below with reference to the drawings as to the configuration when applied to a laparoscopic surgery support system according to the present invention. The present invention is applicable to general endoscopic surgery using an imaging device such as thoracoscope, gastrointestinal endoscope, cystoscope, arthroscope, robotic assisted surgery, spinal endoscope, surgical microscope, neuroendoscope and endoscope, not limited to laparoscopic surgery.

First Embodiment

Figure 1:
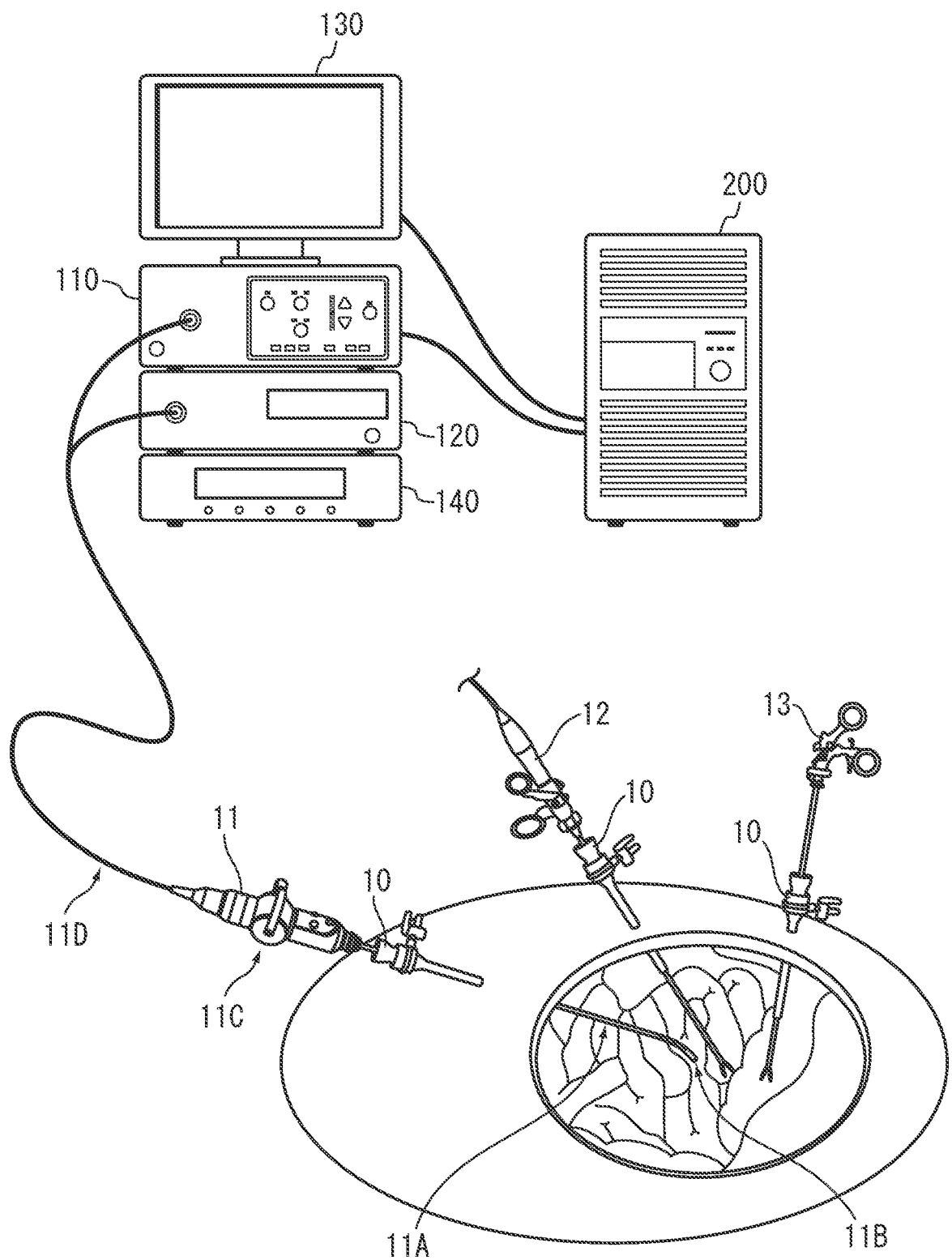
FIG. 1 is a schematic diagram illustrating the rough configuration of a laparoscopic surgery support system according to a first embodiment.

FIG. 1 is a schematic diagram illustrating the rough configuration of a laparoscopic surgery support system according to a first embodiment. In laparoscopic surgery, instead of performing an open abdominal surgery, multiple punctures, which is called trocars 10, are attached to the abdominal wall of the patient, and through the openings attached to the trocars 10, tools such as a laparoscope 11, an energy-based surgical tool 12, and forceps 13 are inserted into the interior of the patient's body. The operator performs procedures such as resection of the affected area using the energy-based surgical tool 12 while viewing in real time the image of the interior of the patient's body (surgical field image) imaged by the laparoscope 11. Surgical tools such as the laparoscope 11, the energy-based surgical tool 12, the forceps 13 and the like are held by the operator or a robot. The operator is here a health care worker involved in the laparoscopic surgery, including a surgeon, an assistant, a nurse and a doctor who monitors the surgery.

The laparoscope 11 has an insertion part 11A to be inserted into the interior of the patient's body, an imaging device 11B integrated in the tip of the insertion part 11A, an operation part 110 provided at the rear end of the insertion part 11A and a universal code 11D used for connection to a camera control unit (CCU) 110 and a light source device 120.

The insertion part 11A of the laparoscope 11 is formed by a rigid tube. The distal end of the rigid tube has a bending portion. The bending mechanism at the bending portion is a well-known mechanism built into the general laparoscope and is so structured as to be bent in four directions, for example, up, down, left, and right, by the operating wire towed in conjunction with the operation via the operation part 11C. The laparoscope 11 may be a rigid endoscope not provided with a bending portion or may be an imaging device not provided with a bending portion or a rigid tube, not limited to a flexible endoscope with the bending portion as described above.

The imaging device 11B has a driver circuit provided with a solid-state imaging device such as CMOS (Complementary Metal Oxide Semiconductor), a timing generator (TG), an analog signal processing circuit (AFE) and the like. The driver circuit of the imaging device 11B takes in RGB signals output for each color from the solid-state imaging device in synchronization with the clock signals output from the TG, and performs necessary processing such as noise reduction, amplification, A/D conversion and the like to generate image data in digital form. The driver circuit of the imaging device 11B transmits the generated image data to the CCU 110 through the universal code 11D.

The operation part 11C is provided with an angle lever and a remote switch to be operated by the operator. The angle lever is an operation tool that accepts operation for bending the bending portion. A bending operation knob, a joystick or the like may be provided instead of the angle lever. The remote switch includes, for example, a selector to switch the display of the observation image between a moving image and a still image and a zoom switch to enlarge or reduce the observation image. The remote switch may be assigned with a predetermined specific function or a function set by the operator.

The operation part 11C may be integrated with an oscillator constructed of a linear resonant actuator, a piezoelectric actuator or the like. In the case where an event to be reported to the operator of the laparoscope 11 occurs, the CCU 110 may report the occurrence of such an event to the operator by vibrating the operation part 11C through activation of the oscillator integrated in the operation part 11C.

A transmission cable for transmitting a control signal output from the CCU 110 to the imaging device 11B and image data output from the imaging device 11B and a light guide for guiding illumination light emitted from the light source device 120 to the distal end of the insertion part 11A are internally disposed through the insertion part 11A, the operation part 11C and the universal cord 11D of the laparoscope 11. The illumination light emitted from the light source device 120 is guided through the light guide to the distal end of the insertion part 11A and is irradiated onto an operation field through an illumination lens provided at the distal end of the insertion part 11A. Though the present embodiment describes the configuration where the light source device 120 is a separate device, the light source device 120 may be integrated in the CCU 110.

The CCU 110 is provided with a control circuit that controls the operation of the imaging device 11B provided in the laparoscope 11 and an image processing circuit that performs processing on the image data input from the imaging device 11B through the universal code 11D. The control circuit is provided with a Central Processing Unit (CPU), a Read Only Memory (ROM), a Random Access Memory (RAM) and the like, and outputs a control signal to the imaging device 11B in response to an operation performed on the various switches on the CCU 110 and the operation part 11C of the laparoscope 11 to control the start and stop of imaging and zooming. The control circuit may be provided with a Graphics Processing Unit (GPU), a Field Programmable Gate Array (FPGA) and the like without being limited to the CPU, the ROM and the RAM. The image processing circuit is provided with a Digital Signal Processor (DSP) and an image memory, and performs appropriate processing such as color separation, color interpolation, gain correction, white balance adjustment, gamma correction and the like on the image data input through the universal cord 11D. The CCU 110 generates frame images used for moving image from the processed image data, and outputs each generated frame image sequentially to the surgical support device 200 described later. The frame rate of the frame images is, for example, 30 FPS (frames per second).

The CCU 110 may generate video data that conforms to a predetermined standard such as NTSC (National television System Committee), PAL (Phase Alternating Line) and DICOM (Digital Imaging and Communication in Medicine). By outputting the generated video data to the display device 130, the CCU 110 can display surgical field images (video) in real time on the display screen of the display device 130. The display device 130 is a monitor provided with a liquid crystal panel, an organic Electro Luminescence (EL) panel or the like. Furthermore, the CCU 110 may output the generated video data to a video recorder 140 to record it to the video recorder 140. The video recorder 140 is provided with a recording device such as a hard disk drive (HDD) that records the video data output from the CCU 110 together with an identifier for identifying each surgery, the date and time of the surgery, the location of the surgery, the patient's name, the operator's name and the like.

The surgical support device 200 generates support information related to laparoscopic surgery based on the image data (that is, the image data of the surgical field image obtained by shooting the surgical field) input from the CCU 110. Specifically, the surgical support device 200 performs processing of recognizing a loose connective tissue part included in the surgical field image and displaying the recognized loose connective tissue part on the display device 130 discernably. Here, the loose connective tissue part included in the surgical field image represents a cluster of pixels corresponding to the loose connective tissue within the surgical field image.

Though the present embodiment describes the configuration where the recognition processing of the loose connective tissue is performed in the surgical support device 200, another configuration may be employed where the CCU 110 is provided with the function similar to the surgical support device 200 to perform the recognition processing of loose connective tissue.

The internal configuration of the surgical support device 200 and the recognition processing and the display processing performed by the surgical support device 200 will be described below.

Figure 2:
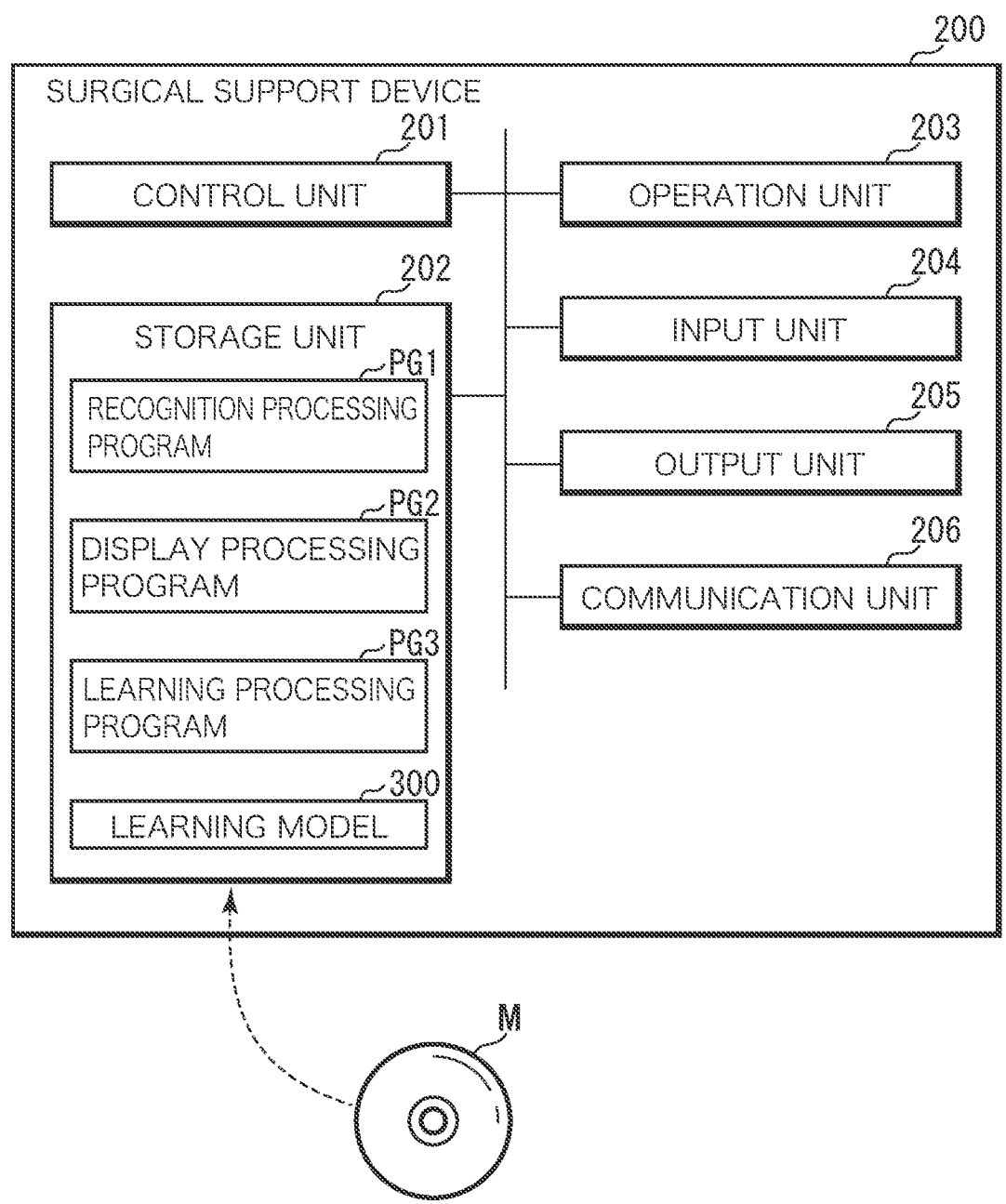
FIG. 2 is a block diagram illustrating the internal configuration of a surgical support device.

FIG. 2 is a block diagram illustrating the internal configuration of the surgical support device 200. The surgical support device 200 is a dedicated or general-purpose computer provided with a control unit 201, a storage unit 202, an operation unit, 203, an input unit 204, an output unit 205, a communication unit 206 and the like. The surgical support device 200 may be a computer installed in an operating room or outside the operating room. In addition, the surgical support device 200 may be a server installed in the hospital where laparoscopic surgery is performed or a server installed outside the hospital. The surgical support device 200 can also be used to support telesurgery.

The control unit 201 is provided with a CPU, a ROM, a RAM and the like. In the ROM provided in the control unit 201, control programs, etc. for controlling the operation of the hardware components provided in the surgical support device 200 are stored. The CPU provided in the control unit 201 executes the control program stored in the ROM and various computer programs stored in the storage unit 202 to be described later to thereby control the operation of each of the hardware components, causing the entire device to function as a surgical support device according to the present application. In the RAM provided in the control unit 201, data used during execution of arithmetic operation or the like is stored.

Though the present embodiment describes the configuration where the control unit 201 is provided with a CPU, a ROM and a RAM, the control unit 201 may have any configuration and may be an arithmetic circuit or a control circuit with one or more GPUs, FPGAs, quantum processors, volatile or non-volatile memory and the like. Furthermore, the control unit 201 may have functions as a clock to output date and time information, a timer to measure the elapsed time from when a measurement start instruction is given to when a measurement end instruction is given and a counter to count the number.

The storage unit 202 is a storage device employing a hard disk, a flash memory and the like. The storage unit 202 stores computer programs to be executed by the control unit 201, various data acquired from the outside and various data generated inside the device.

The computer programs stored in the storage unit 202 includes a recognition processing program PG1 for causing the control unit 201 to execute the processing of recognizing a loose connective tissue part included in the surgical field image, a display processing program PG2 for causing the control unit 201 to execute the processing of displaying support information based on the recognition result on the display unit 130, and a learning processing program PG3 for generating a learning model 300. Note that the recognition processing program PG1 and the display processing program PG2 are not necessarily independent computer programs, and they may be implemented as one computer program. These programs are provided, for example, by a non-transitory recording medium M that readably records computer programs. The recording medium M is a portable memory such as a CD-ROM, a USB memory, an SD (Secure Digital) card or the like. The control unit 201 reads a desired computer program from the recording medium M using a reader (not illustrated) and stores the read computer program on the storage unit 202. Alternatively, the above-mentioned computer program may be provided by communication using the communication unit 206.

Moreover, the storage unit 202 stores the learning model 300 used in the above-mentioned recognition processing program PG1. The learning model 300 is a learning model so trained as to output information on the loose connective tissue part included in the surgical field image in response to input of the surgical field image. The learning model 300 is described by its definition information. The definition information of the learning model 300 includes information on the layers provided in the learning model 300, information on the nodes that constitute each layer and parameters such as weights and biases between the nodes. The learning model 300 stored in the storage unit 202 is a trained learning model that is trained according to a predetermined learning algorithm using as the training data the operation field image obtained by shooting the surgical field and the correct data indicating the loose connective tissue part in the surgical field image. The structure of the learning model 300 and the procedure for generating the learning model 300 are described in detail later.

The operation unit 203 is provided with operation equipment such as a keyboard, a mouse, a touch panel, a non-contact panel, a stylus pen, a voice input device with a microphone or the like. The operation unit 203 accepts an operation by the operator or the like and outputs information on the accepted operation to the control unit 201. The control unit 201 executes appropriate processing in response to operation information input from the operation unit 203. Though the present embodiment describes the configuration where the surgical support device 200 is provided with the operating unit 203, another configuration may be employed where operation is accepted through various equipment such as the CCU 110 connected externally.

The input unit 204 is provided with a connection interface to which input equipment is connected. In the present embodiment, the input equipment connected to the input unit 204 is the CCU 110. The input unit 204 receives input of image data of surgical field images that are imaged by the laparoscope 11 and processed by the CCU 110. The input unit 204 outputs the input image data to the control unit 201. Moreover, the control unit 201 may store the image data acquired from the input unit 204 in the storage unit 202.

The output unit 205 is provided with a connection interface to which output equipment is connected. In the present embodiment, the output equipment connected to the output unit 205 is the display device 130. When generating information that is to be reported to the operator, such as a recognition result using the learning model 300, the control unit 201 outputs the generated information to the display unit 130 through the output unit 205 to display the information on the display unit 130.

The communication unit 206 is provided with a communication interface for sending and receiving various data. The communication interface provided in the communication unit 206 is a communication interface that conforms to wired and wireless communication standards used in Ethernet (registered trademark) and WiFi (registered trademark). When receiving input of data to be sent from the control unit 201, the communication unit 206 sends the data to be transmitted to a designated address. When receiving data sent from an external device, the communication unit 206 outputs the received data to the control unit 201.

Next, the operation field image input to the surgical support device 200 will be described.

Figure 3:
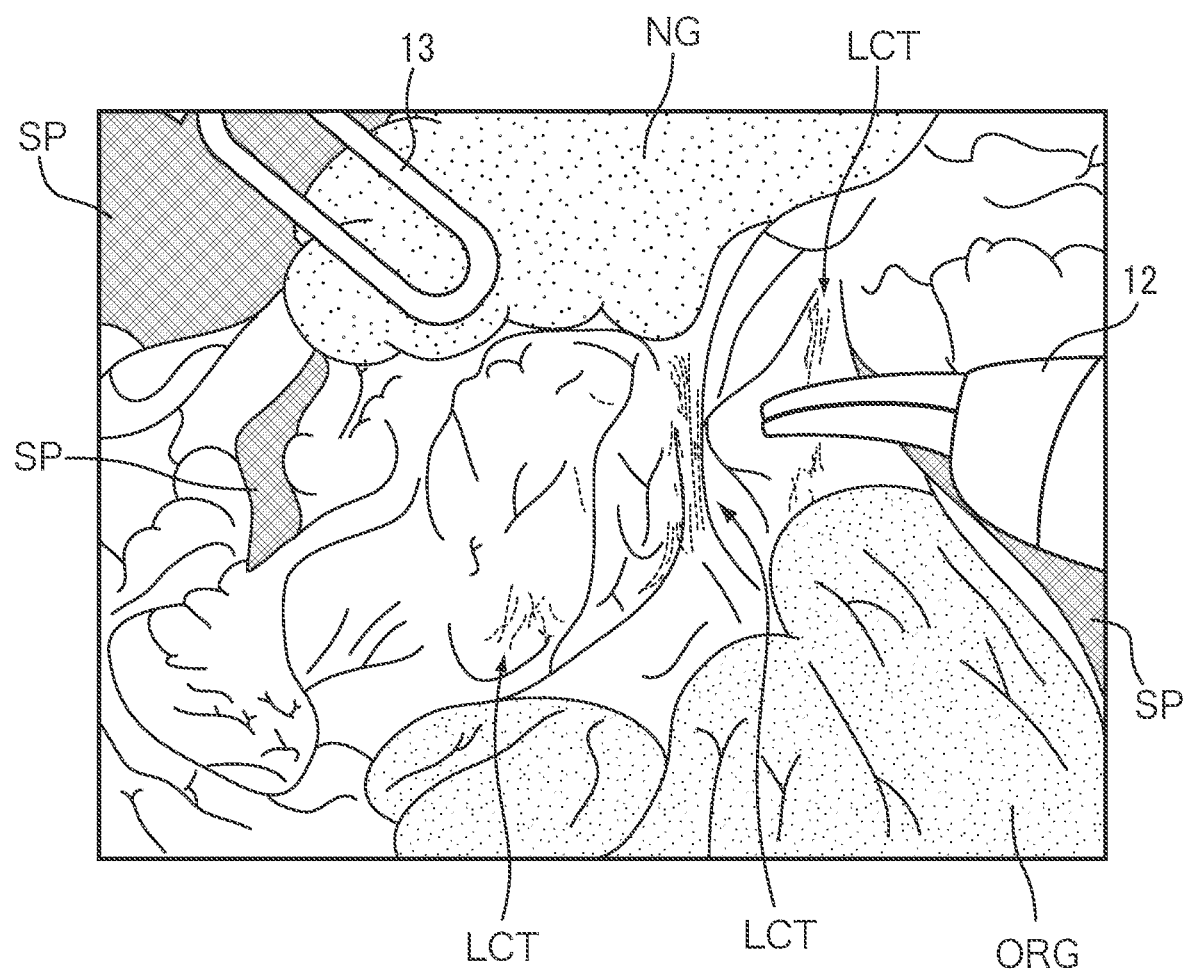
FIG. 3 is a schematic diagram illustrating an example of the operation field image.

FIG. 3 is a schematic diagram illustrating an example of the operation field image. The surgical field image in the present embodiment is an image obtained by shooting the peritoneal cavity of the patient with the laparoscope 11. The surgical field image is not necessarily a raw image output by the imaging device 11B of the laparoscope 11 and may be an image (frame image) processed by the CCU 110 or the like. The surgical field image may also be an image output from the CCU 110 to the display device 130, or may be an image processed by an image processing device (not illustrated) that is attachable to and detachable from the laparoscope 11. Moreover, the surgical field image may be video image already recorded on the video recorder 140.

FIG. 3 illustrates an example of the surgical field image obtained by shooting the situation where laparoscopic surgery is being performed. The surgical field illustrated in FIG. 3 includes the tissue NG including a lesion such as a malignant tumor or the like, the tissue ORG making up of an organ and the loose connective tissue LCT filling the space therebetween. In the present embodiment, the tissue NG is a site that is to be removed from the inside of the body while the tissue ORG is a site that is to be left in the body. In the example in FIG. 3, the loose connective tissue LCT is exposed by the tissue NG being grasped with the forceps 13 and expanded upwards in the drawing. The connective tissue here includes elastic fibers, collagen fibers, fatty tissue and reticular tissue, and fills the space between the tissue. The loose connective tissue LCT is a type of connective tissue having a function of holding organs and epithelium, existing between many organs and tissue, and having protein fibers. A relatively large amount of elastic fiber is called a dense connective tissue (such as ligaments or tendons) and is distinguished from the loose connective tissue. The loose connective tissue LCT is often seen as fibrous during surgery. The direction of the fibers is indefinite and sometimes forms in a net-like pattern as a whole. There are humoral substrates and a variety of cells between the fibers. A large amount of loose connective tissue is identified during surgery, and proper treatment of the loose connective tissue ensures safe progress of the surgery, especially when exfoliation or dissection between organs is performed. In the example illustrated in FIG. 3, the loose connective tissue LCT is illustrated by a dashed line.

Laparoscopic surgery involves surgery to remove lesions such as malignant tumors formed in the patient's body, for example. Here, by holding the tissue NG including the lesion with the forceps 13 and expanding it in the appropriate direction, the operator exposes the loose connective tissue LCT that is present between the tissue NG that contains the lesion and the tissue ORG that is to be left. The operator resects the exposed loose connective tissue LCT using the energy-based surgical tool 12 to exfoliate the tissue NG including the lesion from the tissue ORG to be left.

From the viewpoint of ease of resection of the loose connective tissue LCT, it is preferable that the loose connective tissue LCT to be resected has elasticity. Moreover, it is preferable that a space is formed at the back of the loose connective tissue LCT to be resected to allow the energy-based surgical tool 12 and the forceps 13 to move. In addition, it is preferable that the loose connective tissue LCT to be resected is to be kept under tension. The example in FIG. 3 illustrates the situation where a space SP at the back of the loose connective tissue LCT is present, and at least part thereof is held under tension.

The fibers making up of the loose connective tissue LCT are surrounded by blood vessels, nerves, humoral substrates and various cells. It is thus not always easy for the operator to find the loose connective tissue LCT from the surgical field image. Hence, the surgical support device 200 according to the present embodiment recognizes the loose connective tissue part from the surgical field image using the learning model 300, and outputs support information related to laparoscopic surgery based on the recognition result.

Figure 4:
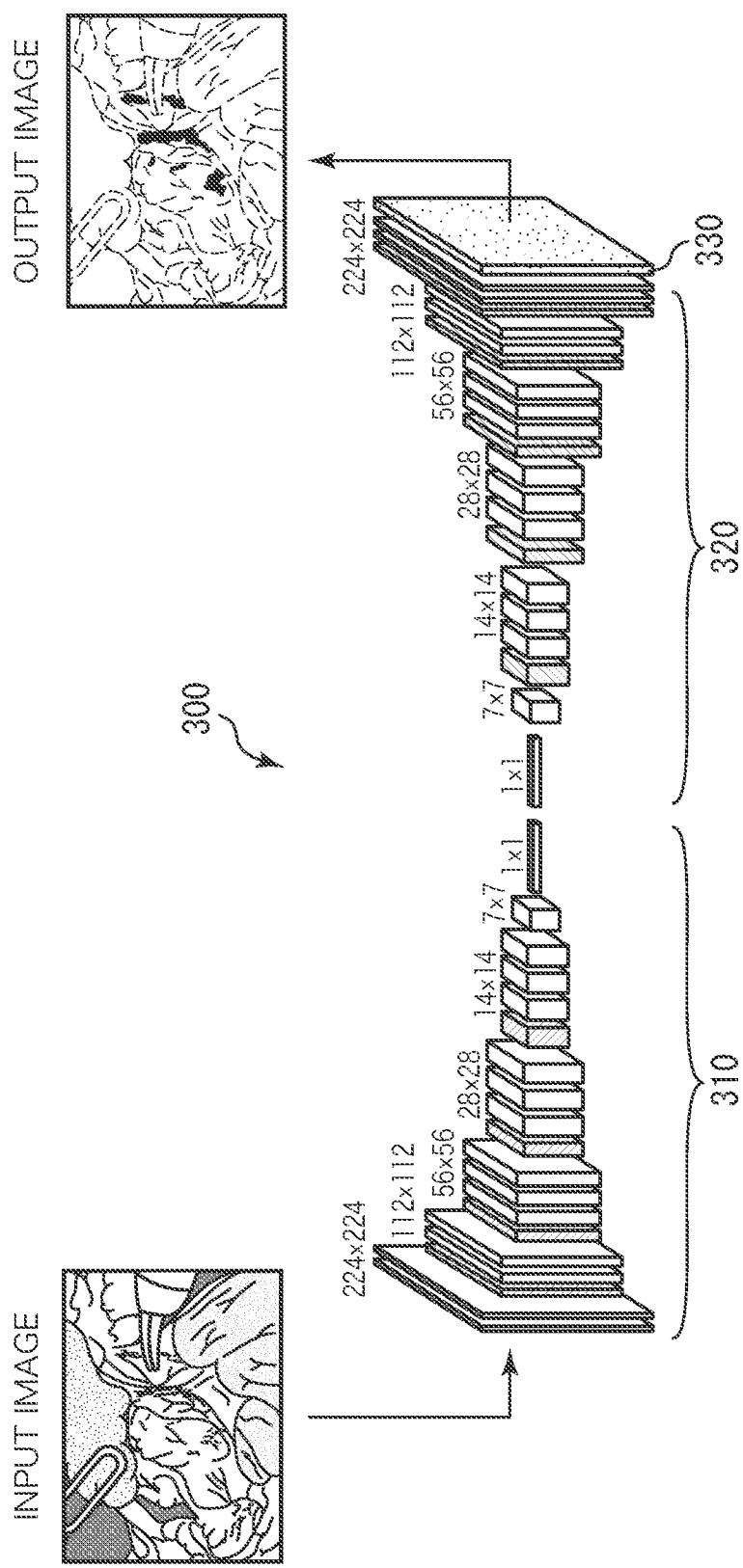
FIG. 4 is a schematic diagram illustrating an example of the configuration of a learning model.

Now, an example of the configuration of the learning model 300 used in the surgical support device 200 will be described. FIG. 4 is a schematic diagram illustrating an example of the configuration of the learning model 300. The learning model 300 is a learning model for performing picture segmentation and constructed by a neural network with convolution layers such as the SegNet. Though FIG. 4 illustrates an example of the configuration of the SegNet, any neural network which can perform picture segmentation may be employed including the Fully Convolutional Network (FCN), the U-shaped Network (U-Net), the Pyramid Scene Parsing Network (PSPNet), not limited to the SegNet, to construct the learning model 300. Instead of the neural networks for picture segmentation, the neural networks for object detection such as You Only Look Once (YOLO) or Single Shot Multi-Box Detector (SSD) may be employed to construct the learning model 300.

In the present embodiment, an input image to be input to the learning model 300 is the operation field image obtained by the laparoscope 11. The learning model 300 is so trained as to output information on the loose connective tissue (i.e., the probability of each pixel belonging to the loose connective tissue) in response to the input of the surgical field image.

The learning model 300 according to the present embodiment includes, for example, an encoder 310, a decoder 320 and a softmax layer 330. The encoder 310 is so configured that convolution layers and pooling layers are alternately arranged. The convolution layer is multi-layered including two or three layers. In the example in FIG. 4, the convolution layer is illustrated without hatching, and the pooling layer is illustrated with hatching.

In the convolution layer, a convolution operation is performed between the input data and a filter having a size specified for each convolution layer (e.g., 3×3 or 5×5). That is, the input values entered at the positions corresponding to the elements of the filter and the weighting factors preset in the filter are multiplied for each element, and the linear sum of the multiplication values for the respective elements is calculated. The set bias is added to the calculated linear sum, and the added value is obtained as the output in the convolution layer. The result of the convolution operation may be converted by the activation function. For example, Rectified Linear Unit (ReLU) can be employed as the activation function. The output of the convolution layer represents a feature map that illustrates the extraction of the features of the input data.

In the pooling layer, a local statistic of the feature map output from the convolution layer, which is an upper layer connected on the input side, is calculated. Specifically, a window of a predetermined size (e.g., 2×2, 3×3) at the position corresponding to the upper layer is set, and the local statistic is calculated from the input values in the window. As the statistic, the maximum value, for example, can be adopted. The size of the feature map output from the pooling layer is reduced (down-sampled) depending on the size of the window. The example in FIG. 4 illustrates that by repeating the arithmetic operations in the convolution layer and the arithmetic operations in the pooling layer, the encoder 310 sequentially down-samples the input image of 224×224 pixels into the feature maps of 112×112 pixels, 56×56 pixels, 28×28 pixels, . . . and 1×1 pixel in this order.

The output of the encoder 310 (a 1×1 feature map in the example in FIG. 4) is input to the decoder 320. The decoder 320 is so configured that deconvolution layers and unpooling layers are alternately arranged. The deconvolution layer is multi-layered including two or three layers. In the example in FIG. 4, the deconvolution layer is represented without hatching, and the unpooling layer is represented with hatching.

In the deconvolution layer, the deconvolution operation is performed on the input feature map. The deconvolution operation is an operation that restores the input feature map to the feature map before the convolution operation, under assumption that the input feature map is the resultant of the convolution operation using a specific filter. This arithmetic operation generates, when the specific filter is represented by a matrix, a feature map for output by multiplying the transposed matrix of this matrix by the input feature map. Note that the result of the arithmetic operation in the deconvolution layer may be converted by the activation function such as ReLU as described above.

The unpooling layers provided in the decoder 320 are placed in a one-to-one correspondence with the pooling layers provided in the encoder 310, and the corresponding pairs each have a substantially identical size. The unpooling layer increases (up-samples) again the size of the feature map that has been down-sampled in the pooling layer in the encoder 310. The example in FIG. 4 illustrates that, by repeating the arithmetic operations in the deconvolution layer and the arithmetic operations in the unpooling layer, the decoder 320 sequentially up-samples the input image of the feature map of 1×1 pixels into the feature maps of 7×7 pixels, 14×14 pixels, . . . 224×224 pixels in this order.

The output of the decoder 320 (the 224×224 feature map in the example in FIG. 4) is input to the softmax layer 330. The softmax layer 330 applies the softmax function to the input values from the deconvolution layer connected on the input side to output the probability of a label identifying the site at each position (pixel). In the present embodiment, a label to identify the loose connective tissue can be set, and whether to belong to the loose connective tissue or not may be identified on a pixel-by-pixel basis. By extracting pixels with a probability of the label output from the softmax layer 330 equal to or more than the threshold (e.g., 50% or more), an image representing the loose connective tissue part (hereinafter referred to as a recognition image) is obtained. The threshold may be stored in the storage unit 202 in advance. The change of the threshold may be accepted through the operation unit 203, and the changed threshold may be stored in the storage unit 202. In this case, the control unit 201 may determine whether or not each pixel belongs to the loose connective tissue using the changed threshold.

Tough in the example illustrated in FIG. 4, a 224-pixel× 224-pixel image is used as the input image to the learning model 300, the size of the input image is not limited to the above-described size and may be set depending on the processing capacity of the surgical support device 200 and the size of the surgical field image obtained from the laparoscope 11. In addition, the input image to the learning model 300 is not necessarily the entire surgical field image obtained from the laparoscope 11, but may be a partial image generated by cutting out a focused region of the surgical field image. Since the focused region including the target to be treated is often located near the center of the surgical field image, for example, a partial image may be used that is obtained by cutting out the near center of the surgical field image in a rectangular shape so that the obtained image is half the size of the original. By reducing the size of the image input to the learning model 300, the recognition accuracy can be enhanced while increasing the processing speed.

The learning model 300 may be configured to recognize a part or the entire fibrous loose connective tissue as a single cluster. That is, the learning model 300 may be configured to recognize each piece of loose connective tissue as a single cluster, or to recognize more than the predetermined number of loose connective tissue (e.g., 10) as a single cluster.

Figure 5:
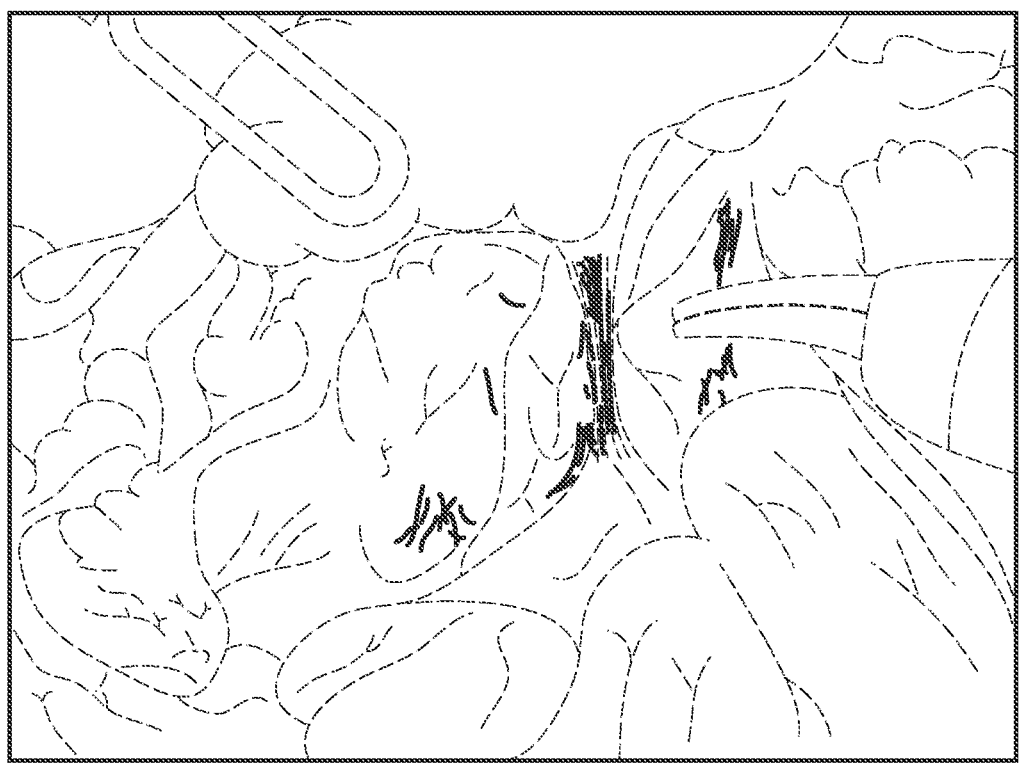
FIG. 5 is a schematic diagram illustrating a recognition result by the learning model.

FIG. 5 is a schematic diagram illustrating a recognition result by the learning model 300. In the example in FIG. 5, the partial loose connective tissue part that is recognized using the learning model 300 is represented in solid lines, and the organs and tissue other than the partial loose connective tissue part are represented in dashed lines for reference. The control unit 201 of the surgical support device 200 generates a recognition image of the loose connective tissue in order to discernably display the recognized loose connective tissue part. The recognition image is an image of the same size as the surgical field image where a specific color is assigned to the pixels recognized as the loose connective tissue. The color to be assigned to the pixels corresponding to the loose connective tissue is preferably a color not present in the human body so as to be discernable from organs and blood vessels. The color not present in the human body is cold colors (blue tones) such as blue or light blue. In addition, information indicating transparency is added to each of the pixels that constitute the recognition image. The value indicative of being opaque (opaque value) is set to each pixel recognized as the loose connective tissue while the value indicative of being transparent (transparent value) is set to each of the rest of the pixels. The recognition image thus generated is superimposed on the surgical field image to allow the loose connective tissue part to be displayed in a specific color on the surgical field image. The control unit 201 may adjust the parameters such as hue, brightness, saturation, transparency and the like in order to visibly display the recognition image of the loose connective tissue.

The operation of the surgical support device 200 will be described below.

The surgical support device 200 generates the learning model 300 in the learning phase before the start of the implementation, for example. As a preparation stage for generating the learning model 300, annotation is carried out by manually segmenting the loose connective tissue part from the surgical field images obtained by the laparoscope 11 in the present embodiment. It is noted that surgical field images recorded on the video recorder 140 may be used for annotation.

When annotation is carried out, the operator (expert such as a doctor) finds the loose connective tissue that is present between the tissue containing the lesion (the site to be removed) and the organ (the site to be left) and is in an easily resectable condition while causing the display device 130 to chronologically display the surgical field images. Specifically, by expanding the tissue containing the lesion, the operator finds the exposed loose connective tissue. The loose connective tissue to be annotated is preferably a part with elasticity, for example. Furthermore, the loose connective tissue to be annotated is preferably kept under tension. Moreover, it is preferable that a space is provided at the back of the loose connective tissue to be annotated so as to allow the energy-based surgical tool 12 and the forceps 13 to move. In the case of finding the loose connective tissue in an easily resectable condition, the operator performs annotation by selecting a part corresponding to the loose connective tissue on a pixel-by-pixel basis in the surgical field image using a mouse and a stylus pen provided in the operation unit 203. A pattern of the loose connective tissue suitable for learning is selected to increase the amount of data by processing such as perspective transform and mirror operation. In addition, as the learning progresses, the amount of data can be increased by diverting the recognition results by the learning model 300. By performing the annotation described above, the learning model 300 is configured to recognize the fibrous part at a stage when the loose connective tissue with elasticity makes transitions from a state before tension to a state under tension.

In the present embodiment, about 4,000 sheets of surgical field images are annotated to increase the amount of data. Finally, about 20,000 pairs of training data are prepared each consisting of a pair of surgical field image and correct data illustrating the loose connective tissue part. The training data is stored in the storage device (e.g., the storage unit 202 of the surgical support device 200).

Figure 6:
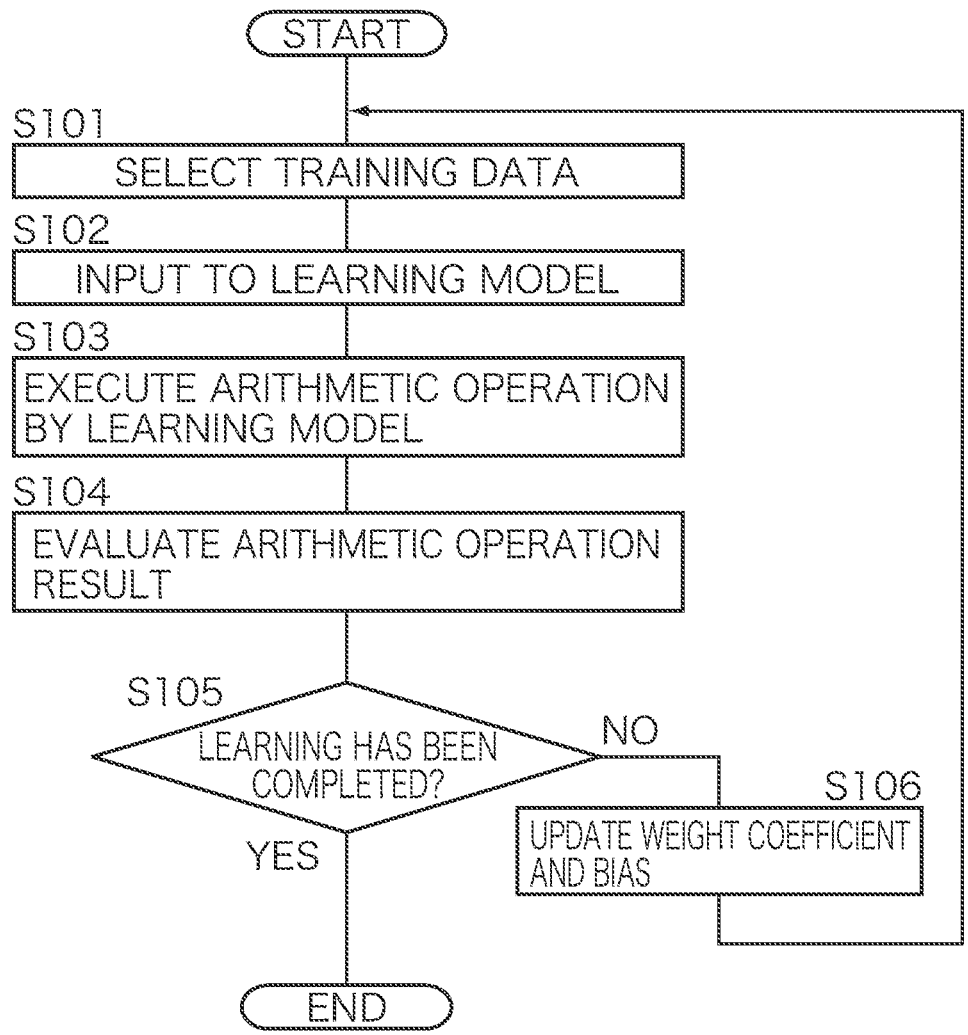
FIG. 6 is a flowchart illustrating the procedure of generating a learning model.

FIG. 6 is a flowchart illustrating the procedure of generating the learning model 300. The control unit 201 of the surgical support device 200 reads the learning processing program PG3 from the memory unit 202 and performs the following steps to thereby generate the learning model 300.

In the pre-training stage, the initial value is assumed to be given to the definition information describing the learning model 300.

The control unit 201 first accesses the storage unit 202 and selects a pair of training data to be used for training (step S101). The control unit 201 inputs the surgical field image included in the selected training data to the learning model 300 (step S102) and performs arithmetic operation by the learning model 300 (step S103). In other words, the control unit 201 generates a feature map from the input surgical field image, and performs arithmetic operations using the encoder 310 to sequentially down-sample the generated feature map, arithmetic operations using the decoder 320 to sequentially up-sample the feature map input from the encoder 310 and arithmetic operation by the softmax layer 330 to identify each pixel of the feature map finally obtained from the decoder 320.

The control unit 201 may acquire the result of the arithmetic operations from the learning model 300 and evaluate the obtained result of the arithmetic operations (step S104). For example, the control unit 201 may evaluate the operation result by calculating the similarity between the image data of the loose connective tissue part obtained as a result of the arithmetic operations and the correct data included in the training data. The similarity is calculated by the Jaccard coefficient, for example. The Jaccard coefficient is given as A∩B/A∪B×100 (%) when the loose connective tissue part extracted by the learning model 300 is A, and the loose connective tissue part included in the correct data is B. Instead of the Jaccard coefficient, the Dice coefficient and the Simpson coefficient may be calculated. Alternatively, using other existing methods, the similarity may be calculated.

The control unit 201 determines whether or not learning is finished based on the evaluation of the results of the arithmetic operation (step S105). The control unit 201 can determine that learning is finished when the similarity equal to or more than the preset threshold is obtained.

When determining that learning is not finished (S105: NO), the control unit 201 sequentially updates the weighting factors and biases in each layer of the earning model 300 from the input side to the output side using an error back propagation method (step S106). After updating the weighting factors and biases in each layer, the control unit 201 returns the processing to step S101 to perform again the processing from steps S101 to S105.

When determining that learning is finished at step S105 (S105: YES), the control unit 201 ends the processing according to this flowchart since it can obtain the trained learning model 300.

Though the present embodiment describes the configuration where the learning model 300 is generated by the surgical support device 200, the learning model 300 may be generated by an external computer. The surgical support device 200 may obtain the learning model 300 generated by the external computer through any means such as communication or the like and store the obtained learning model 300 in the storage unit 202.

Figure 7:
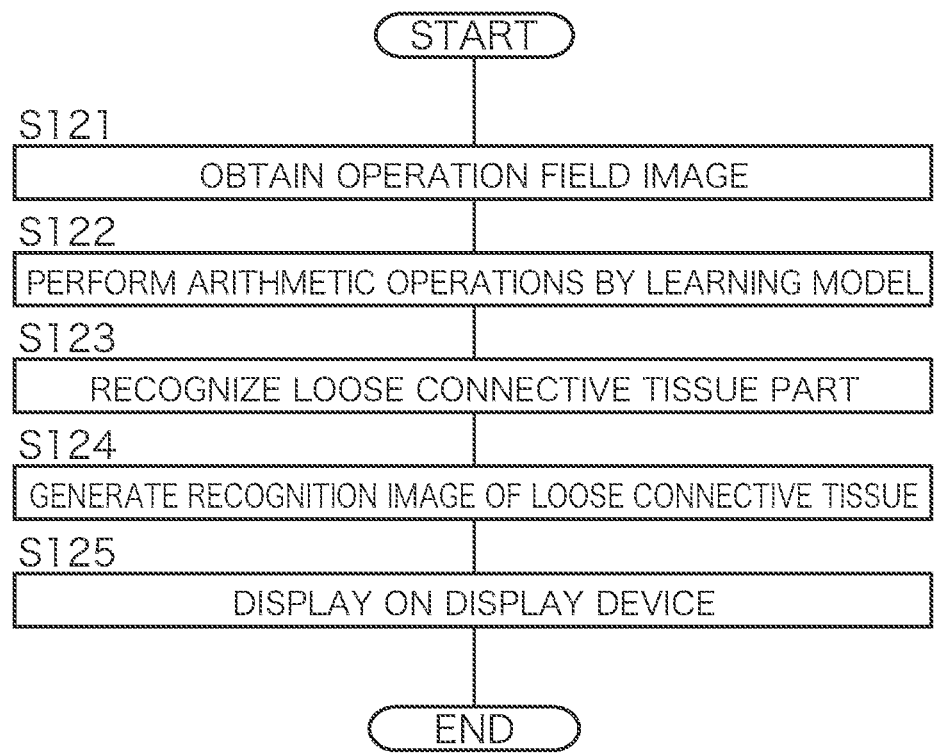
FIG. 7 is a flowchart illustrating the procedure of executing a surgery support.

The surgical support device 200 performs surgical support in the implementation phase after generation of the learning model 300. FIG. 7 is a flowchart illustrating the procedure of executing a surgery support. The control unit 201 of the surgical support device 200 reads and executes the recognition processing program PG1 and the display processing program PG2 from the storage unit 202 to thereby perform the following procedure. When laparoscopic surgery is started, surgical field images obtained by shooting the surgical field with the imaging device 11B of the laparoscope 11 are output to the CCU 110 through the universal code 11D at any time. The control unit 201 of the surgical support device 200 acquires the surgical field image output from the CCU 110 by the input unit 204 (step S121). The control unit 201 performs the following processing each time it acquires the operation field image.

The control unit 201 inputs the acquired surgical field image to the learning model 300 to perform an arithmetic operation using the learning model 300 (step S122) and recognizes the loose connective tissue part included in the surgical field image (step S123). In other words, the control unit 201 generates a feature map from the input surgical field image, and performs arithmetic operations using the encoder 310 to sequentially down-sample the generated feature map, arithmetic operations using the decoder 320 to sequentially up-sample the feature map input from the encoder 310 and arithmetic operation by the softmax layer 330 to identify each pixel of the feature map finally obtained from the decoder 320. Moreover, the control unit 201 recognizes each pixel with a probability of label output from the softmax layer 330 equal to or more than threshold (e.g., 50% or more) as the loose connective tissue part.

The control unit 201 generates a recognition image of the loose connective tissue in order to discernably display the loose connective tissue part recognized using the learning model 300 (step S124). As described above, the control unit 201 may assign a color not present in the human body (e.g., cold colors (blue tones) such as blue or light blue) to the pixels recognized as the loose connective and may set transparency that allows transparent background to the pixels other than the loose connective tissue.

The control unit 201 outputs the recognition image of the loose connective tissue generated at step S124 together with the surgical field image acquired at step S121 to the display device 130 through the output unit 205 to display on the display device the recognition image superimposed on the surgical field image (step S125). Thus, the loose connective tissue part recognized using the learning model 300 is displayed in a specific color on the surgical field image. Moreover, the control unit 201 may display on the display device 130 a message indicating that the loose connective tissue represented by a specific color is the site to be resected.

Figure 8:
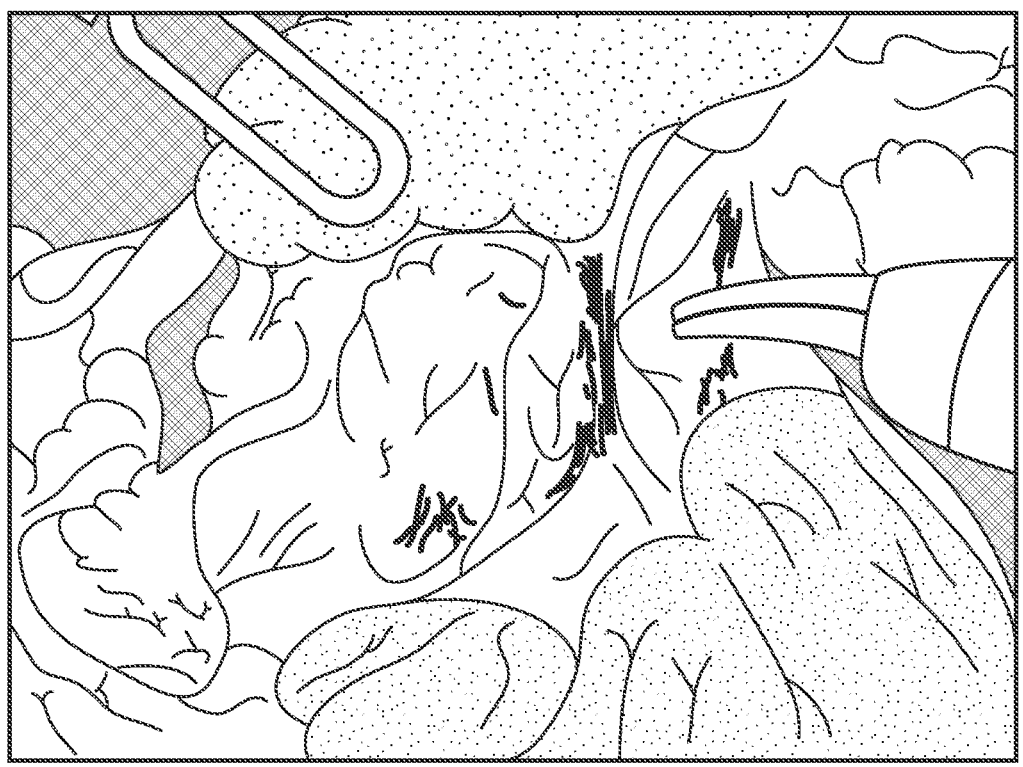
FIG. 8 is a schematic diagram illustrating a display example of a display device.

FIG. 8 is a schematic diagram illustrating a display example of the display device 130. For the convenience of drawing creation, the loose connective tissue part recognized using the learning model 300 is represented in heavy solid lines in the display example illustrated in FIG. 8. In practice, the part corresponding to the loose connective tissue is painted with a color not present in the human body such as blue or light blue on a pixel-by-pixel basis, and thus the operator can clearly identify the loose connective tissue by viewing the display screen of the display device 130 and grasp the site to be resected.

Though the present embodiment describes the configuration where the recognition result of the loose connective tissue using the learning model 300 is displayed on the display device 130, by provision of a display device separate from the display device 130, the surgical field image may be displayed on the display device 130 while the recognition image using the learning model 300 may be displayed on the separate display device. Moreover, the surgical field image may be displayed in an area within the screen of the display device 130 while the recognition result using the learning model 300 may be displayed in a different area within the same screen.

Though the present embodiment describes the configuration where the loose connective tissue part recognized by the learning model 300 is displayed on the display device 130, the line crossing the recognized loose connective tissue part may be displayed as a recommended line for resection on the display device 130.

Furthermore, in the present embodiment, the line recommended for resection may be estimated by recognizing the loose connective tissue part using the learning model 300. Thus, when a surgical robot is connected to the surgical support device 200, control signals to instruct resection of the loose connective tissue may be output to the surgical robot.

Moreover, the surgical support device 200 may set the recommended range for resection out of the recognized loose connective tissue part and display on the display device 130 the recommended range having set in a different display manner (color, hue, brightness, saturation, transparency and the like). That is, the transparency may be changed in order that the loose connective tissue part corresponding to the recommended range can be displayed while the loose connective tissue part other than the recommended range cannot be displayed. Alternatively, the display color may be changed between the loose connective tissue part corresponding to the recommended range and the loose connective tissue part other than the recommended range.

The recommended range can arbitrarily be set. For example, when recognizing the loose connective tissue between the lesion tissue (the site to be removed by endoscopic surgery) and the normal tissue (the site to be left by endoscopic surgery), the surgical support device 200 may divide the part containing the loose connective tissue into three ranges including the range closer to the lesion tissue, the range closer to the normal tissue and the range between both of them and then set one of the three ranges as the recommended range. The surgical support device 200 may calculate the length of the loose connective tissue in the longitudinal direction (the direction in which the fibers extend) in the surgical field image and may split the loose connective tissue such that the length is divided by three, for example. It should be noted that the number of divided ranges may be two or more, not necessarily three.

The surgical support device 200 may set the recommended range depending on the degree of progression of the lesion. For example, when the degree of progression of the lesion is high, the surgical support device 200 may set the range closer to the normal tissue as a recommended range in order to gain a large margin. In contrast, when the degree of progression of the lesion is low, the surgical support device 200 may set the range closer to the lesion tissue as a recommended range in order to reduce the range to be resected. The information on the degree of progression of the lesion may be entered in advance through the operation unit 203 or the communication unit 206.

In addition, the surgical support device 200 may set a recommended range depending on the operator. For example, when the operator prefers resection of the range closer to the lesion tissue, the surgical support device 200 may set the range closer to the lesion tissue as a recommended range. In contrast, when the operator prefers resection of the range closer to the normal tissue, the surgical support device 200 may set the range closer to the normal tissue as a recommended range. The range to be resected preferred by the operator may be set in advance through the operation unit 203 or the communication unit 206.

As described above, in the present embodiment, the structure of the loose connective tissue can be recognized using the learning model 300, and the loose connective tissue can discernably be displayed on a pixel-by-pixel basis, which can provide visual support for laparoscopic surgery. The images generated by the surgical support device 200 can be used not only for surgical support, but also for educational support of residents, and can also be used for evaluation of laparoscopic surgery. For example, laparoscopic surgery can be evaluated by comparing the images recorded on the video recorder 140 during the surgery with the images generated by the surgical support device 200 and determining whether or not the site resected by the laparoscopic surgery is appropriate.

Second Embodiment

The second embodiment describes a configuration where the display manner is changed according to the confidence obtained when loose connective tissue is recognized.

The entire configuration of the laparoscopic surgery support system and the internal configuration of the surgical support device 200 are similar to those of the first embodiment, and thus the description thereof will not be made here.

Referring to the probability output from the softmax layer 330 of the learning model 300, the surgical support device 200 according to the above-mentioned first embodiment generates a recognition image representing the loose connective tissue by assigning a specific color (e.g., cold colors) and the transparency 1 (opaque) to a pixel with a probability equal to or more than the threshold (e.g., 50% or more) and assigning the transparency 0 (fully transparent) to a pixel with a probability less than the threshold. The surgical support device 200 outputs the recognition image and displays the recognition image superimposed on the surgical field image to allow uniform display (overlay display) of the loose connective tissue part.

Meanwhile, the surgical support device 200 according to the second embodiment sets a specific color (e.g., cold colors) to each pixel of the recognition image, and sets the transparency to each pixel according to the probability (confidence) output from the softmax layer 330 of the learning model 300, to generate a recognition image of the loose connective tissue part. More specifically, the surgical support device 200 sets the transparency of each pixel such that the higher the confidence is, the lower the transparency is, and the lower the confidence is, the higher the transparency is. For example, the transparency when the confidence is X % can be set to X/100. The surgical support device 200 outputs the generated recognition image and displays the recognition image superimposed on the surgical field image to realize a display depending on the confidence (soft map display).

Figure 9:
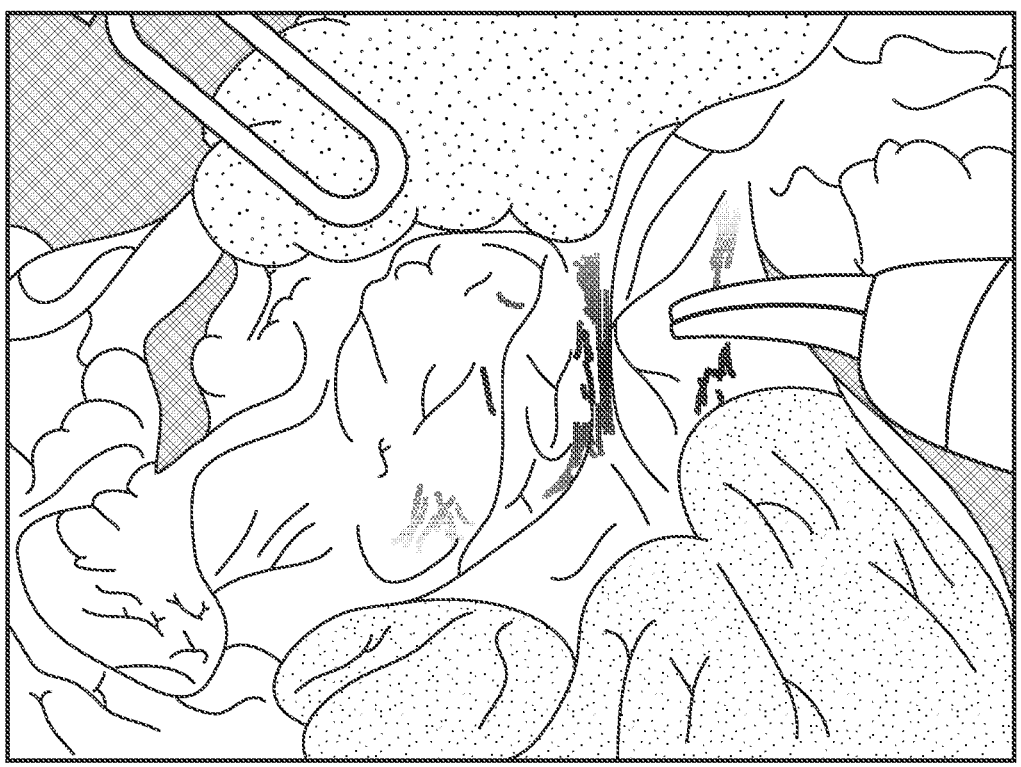
FIG. 9 is a schematic diagram illustrating a display example of a recognition image according to a second embodiment.

FIG. 9 is a schematic diagram illustrating a display example of the recognition image according to the second embodiment. For the convenience of drawing, the degree of transparency is represented by the color density. That is, in the example in FIG. 9, the recognition image is illustrated such that the loose connective tissue part with a high confidence has a high color density and the loose connective tissue part with a low confidence has a low color density.

In the second embodiment, the loose connective tissue part with relatively high confidence is clearly displayed, so that information useful for conducting traction operations and exfoliation operations can precisely be presented to the operator.

Though the second embodiment describes the configuration where the transparency is changed depending on the confidence, the color, hue, saturation and brightness may be changed depending on the confidence.

Third Embodiment

The third embodiment describes the configuration where the site that is to be removed by laparoscopic surgery and the site that is to be left by the laparoscopic surgery are recognized and displayed together with the loose connective tissue part included in the surgical field image.

It is noted that the entire configuration of the laparoscopic surgery support system and the internal configuration of the surgical support device 200 are similar to those of the first embodiment, and thus the description thereof will not be made here.

Figure 10:
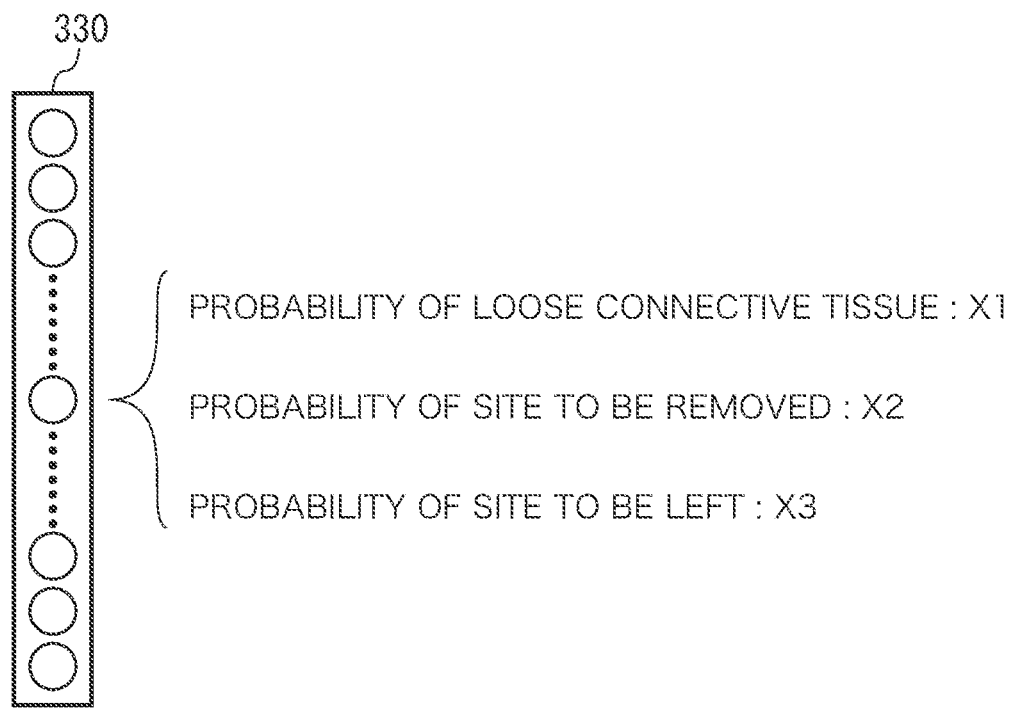
FIG. 10 illustrates the configuration of a softmax layer of a learning model according to a third embodiment.

FIG. 10 illustrates the configuration of the softmax layer 330 of the learning model 300 according to the third embodiment. FIG. 10 illustrates the softmax layer 330 one-dimensionally for the sake of simplicity. The softmax layer 330 of the learning model 300 outputs the probability of the label identifying the site of the feature map for each pixel as described in the first embodiment. The third embodiment allows setting of a label to identify the loose connective tissue, a label to identify the site to be removed (tissue NG in the example of FIG. 3), and a label to identify the site to be left (tissue ORG in the example of FIG. 3). The control unit 201 of the surgical support device 200 recognizes the pixel as the loose connective tissue when the probability of the label identifying the loose connective tissue is equal to or more than the threshold value. Likewise, the control unit 201 recognizes the pixel as a site to be removed when the probability of the label identifying the site to be removed is equal to or more than the threshold, and recognizes the pixel as a site to be left when the probability of the label identifying the site to be left is equal to or more than the threshold.

The learning model 300 to obtain such recognition results is generated by being trained with a large number of training data prepared in advance. In the third embodiment, pairs of the surgical field image and the correct data obtained by performing segmentation on the tissue part that contains a lesion such as malignant tumors or the like, the tissue part that makes up of an organ and the loose connective tissue part that binds these tissue parts are used as training data. The method of generating the learning model 300 is similar to that of the first embodiment, and thus the description thereof will not be made here.

Figure 11:
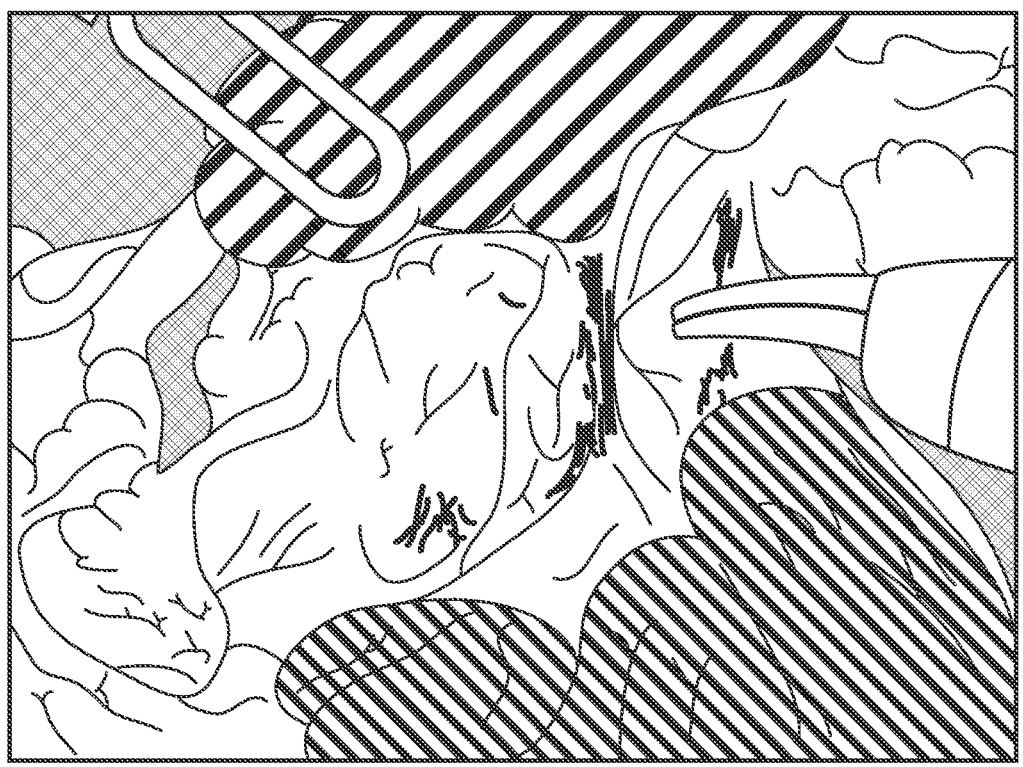
FIG. 11 is a schematic diagram illustrating a display example according to the third embodiment.

FIG. 11 is a schematic diagram illustrating a display example according to the third embodiment. The surgical support device 200 according to the third embodiment recognizes the loose connective tissue part, the region to be removed by laparoscopic surgery (tissue part that contains a lesion such as malignant tumor or the like) and the region to be left by the laparoscopic surgery (tissue part that makes up of an organ) that are included in the surgical field image using the learning model 300 and displays them distinguishably on the display device 130. In the display example in FIG. 11, the loose connective tissue part recognized using the learning model 300 is represented in heavy solid lines, and the region to be removed by laparoscopic surgery (the upper region of the loose connective tissue) and the region to be left (the lower region of the loose connective tissue) are represented in different hatchings. In practice, the control unit 201 may assign a color not present in the human body such as blue or light blue to the part corresponding to the loose connective tissue on a pixel-by-pixel basis, and may display the region that is to be removed and the region that is to be left by laparoscopic surgery in different colors. By browsing the display screen of the display device 130, the operator can clearly identify the loose connective tissue that binds to the site to be removed by laparoscopic surgery and the site to be left by laparoscopic surgery.

Instead of the configuration where the region to be removed and the region to be left by laparoscopic surgery are entirely colored, only the outlines of these regions may be colored and displayed. Instead of the configuration where the region to be removed and the region to be left by laparoscopic surgery are both colored, only one of them may be colored.

As described above, in the third embodiment, along with the loose connective tissue part recognized by the learning model 300, at least one of the region to be removed by laparoscopic surgery and the region to be left by laparoscopic surgery can discernably be displayed to the operator, so that the information on the loose connective tissue part to be resected can clearly be presented to the operator.

Fourth Embodiment

The fourth embodiment describes the configuration where the loose connective tissue part is displayed at the timing when the operator provides instructions.

The surgical support device 200 according to the fourth embodiment switches between display and non-display of the loose connective tissue part according to the operator's switching operation. That is, the surgical support device 200 displays the loose connective tissue part on the display device 130 only when a specific switch (hereafter referred to as a selector) is operated. Here, the selector for switching between display and non-display of the loose connective tissue part may be a switch provided in the operation part 11C of the laparoscope 11 or a foot switch not illustrated in the drawing. The operation information indicating that the selector is operated is reported to the CCU 110 through the universal code 11D, for example, and then reported to the surgical support device 200 via the CCU 110.

Figure 12A:
FIGS. 12A and 12B are a schematic diagram illustrating a display example according to a fourth embodiment.
Figure 12B:
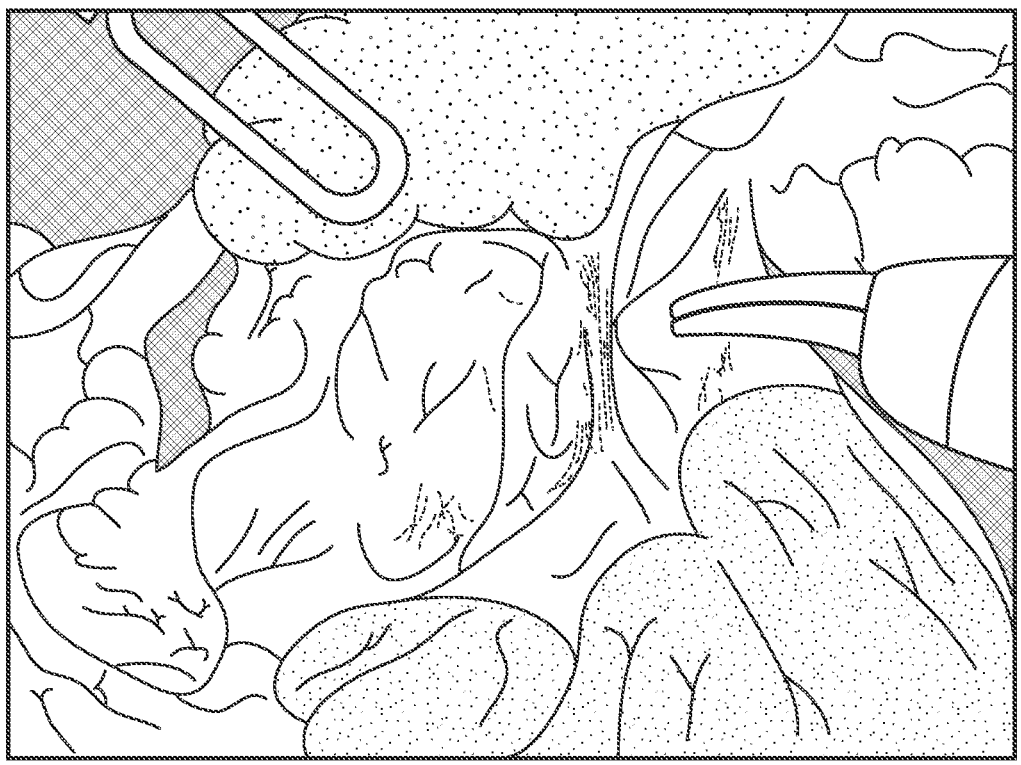

FIGS. 12A and 12B are a schematic diagram illustrating a display example according to the fourth embodiment. FIG. 12A illustrates a display example when the selector is operated, and FIG. 12B illustrates a display example when the selector is not operated. In the fourth embodiment, the loose connective tissue part is displayed on the display device 130 as illustrated in FIG. 12A only when the selector is operated. The display manner of the loose connective tissue part is similar to that in the first embodiment, and the part corresponding to the loose connective tissue may be only necessary to be displayed in a color not present in the human body such as blue or light blue on the pixel-by-pixel basis.

Figure 13:
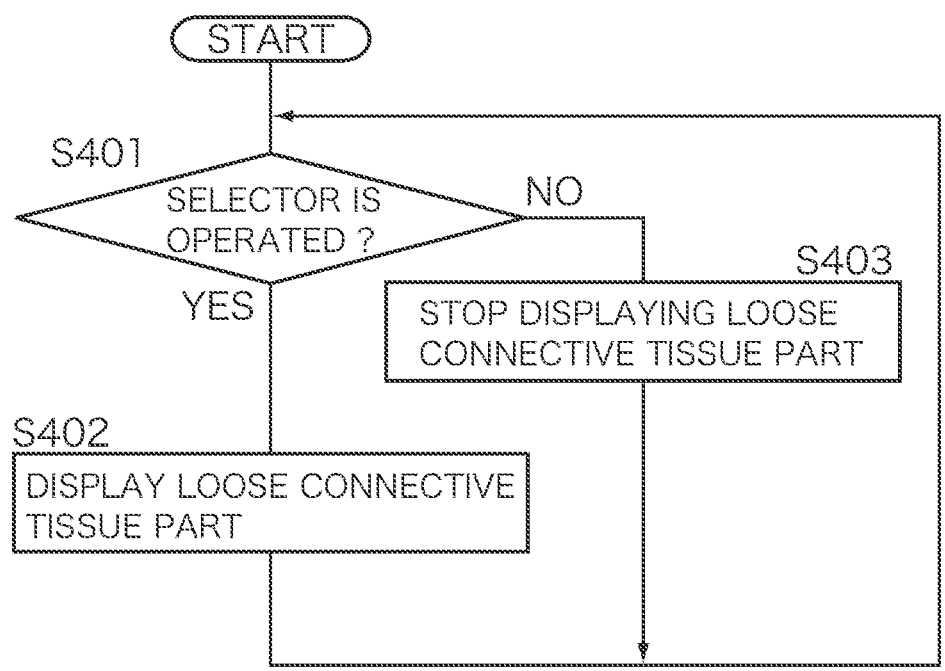
FIG. 13 is a flowchart illustrating a display switching procedure according to the fourth embodiment.

FIG. 13 is a flowchart illustrating a display switching procedure according to the fourth embodiment. The control unit 201 of the surgical support device 200 determines whether or not the selector is operated based on the operation information reported from the CCU 110 (step S401).

When determining that the selector is operated (S401: YES), the control unit 201 displays the loose connective tissue part (step S402). In order to discernably display the loose connective tissue part recognized using the learning model 300, the control unit 201 generates a recognition image for which a specific color is assigned to the pixels of the corresponding part, and transparency that allows transparent background is set to the pixels other than the loose connective tissue part. The control unit 201 can output the generated recognition image along with the surgical field image to the display device 130 and display the recognition image superimposed on the surgical field image to allow display of the loose connective tissue part.

When it is determined that the selector is not operated (S401: NO), the control unit 201 stops displaying the loose connective tissue part (step S403). The control unit 201 may set such transparency that allows transparent background for the pixels corresponding to the recognized loose connective tissue part as well in order to stop displaying the loose connective tissue part. The control unit 201 outputs the generated recognition image along with the surgical field image to the display device 130 and displays the recognition image superimposed on the surgical field image, enabling non-display of the loose connective tissue part. Instead of the configuration where the loose connective tissue part is not displayed by changing the transparency, the output of the recognition image may be stopped.

As described above, in the fourth embodiment, the operator can display the loose connective tissue part at the timing desired by the operation and does not display it at other times.

Though the present embodiment describes the configuration where the loose connective tissue part is displayed when the selector is operated and is not displayed when not operated, the loose connective tissue part may not be displayed when the selector is operated and may be displayed when not operated. The selector to switch between display and non-display of the loose connective tissue part may be provided at the CCU 110. In addition, switching between display and non-display of the loose connective tissue part may be made by operating a touch panel provided on the display device 130 or the operation unit 203 provided on the surgery support device 200. Though the present embodiment describes the configuration where display is switched using a physical switch, display may be switched according to voice input by the operator. Thus, a voice input unit such as a microphone or the like may be provided at the operation unit 11C of the laparoscope 11 or the CCU 110.

Fifth Embodiment

The fifth embodiment describes the configuration where switching is made between display and non-display of the loose connective tissue part depending on the status of laparoscopic surgery.

Depending on the operating speed of the surgical support device 200, there may be a time lag in the processing of recognizing the loose connective tissue. Hence, when the loose connective tissue part recognized using the learning model 300 is displayed while the site including the lesion is expanded using the forceps 13 or while the energy-based surgical tool 12 is moved, misalignment may be produced between the displayed loose connective tissue part and the loose connective tissue actually located. Hence, the surgical support device 200 according to the fifth embodiment displays the loose connective tissue part in the case where the target site of the laparoscopic surgery is not moved, and does not display the loose connective tissue part in the case where the energy-based surgical tool 12 starts to move.

Figure 14:
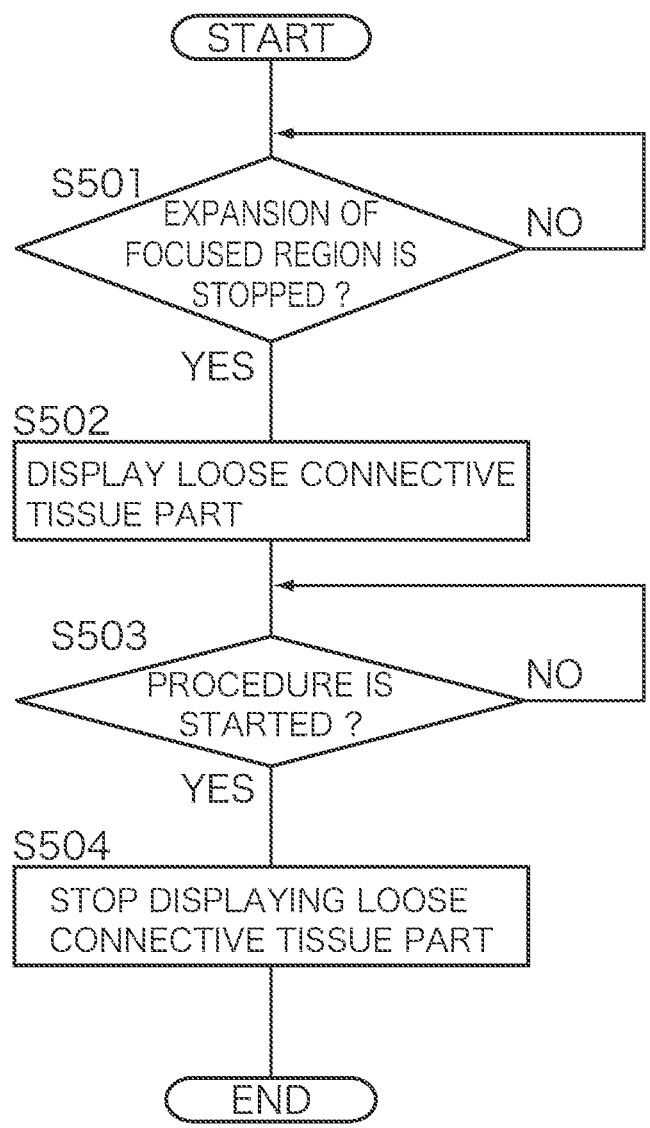
FIG. 14 is a flowchart illustrating a display switching procedure according to a fifth embodiment.

FIG. 14 is a flowchart illustrating a display switching procedure according to the fifth embodiment. This flowchart describes the display switching procedure performed when the loose connective tissue is resected with the energy-based surgical tool 12 after the site including the lesion is expanded using the forceps 13 to expose the loose connective tissue.

The control unit 201 of the surgical support device 200 determines whether or not the expansion of the focused region is stopped based on the surgical field images sequentially input from the input unit 204 (step S501). For example, the control unit 201 may determine whether or not the expansion of the focused region is stopped by generating an optical flow based on the surgical field image sequentially input from the input unit 204. When the expansion of the focused region is not stopped (S501: NO), the control unit 201 is held on standby until the expansion of the target site is stopped because the loose connective tissue may be moved with the expansion of the target site. Though the present embodiment describes the configuration where whether or not the expansion of the focused region is stopped is determined, whether or not the surgical tool (e.g., forceps 13) to expand the focused region is stopped may be determined. In addition, the entire surgical field image is not stopped, but whether or not a preset area (e.g., the area near the center of the surgical field image) is stopped may be determined.

When determining that the expansion of the focused region is stopped (S501: YES), the control unit 201 displays the loose connective tissue part (step S502). When the expansion of the focused region is stopped, the loose connective tissue is considered to be stationary, and thus the displayed position is less likely to be displaced even when the recognized loose connective tissue part is displayed. In order to discernably display the loose connective tissue part recognized using the learning model 300, the control unit 201 generates a recognition image for which a specific color is assigned to the pixels of the corresponding part, and transparency that allows transparent background is set to the pixels other than the loose connective tissue part. The control unit 201 can output the generated recognition image along with the surgical field image to the display device 130, and display the recognition image superimposed on the surgical field image to allow display of the loose connective tissue part.

Next, the control unit 20 determines whether or not the procedure is started (step S503). The control unit 201 can determine whether or not the procedure is started by generating an optical flow and determining whether or not the energy-based surgical tool 12 starts to move as in step S501. When the procedure is not started (S503: NO), the control unit 201 is held on standby until the procedure is started, that is, until the energy-based surgical tool 12 moves to start while maintaining display of the loose connective tissue part.

When determining that the procedure is started (S503: YES), the control unit 201 stops displaying the loose connective tissue part (step S504). The control unit 201 may set such transparency that allows transparent background for the pixels corresponding to the recognized loose connective tissue part as well in order to stop displaying the loose connective tissue part. The control unit 201 enables non-display of the loose connective tissue part by outputting the generated recognition image along with the surgical field image to the display device 130 and by displaying the recognition image superimposed on the surgical field image. Instead of the configuration where the loose connective tissue part is not displayed by changing the transparency, output of the recognition image may be stopped.

As described above, in the fifth embodiment, since the loose connective tissue part is displayed until the expansion of the target site is stopped and the procedure starts, images that do not cause discomfort due to the time lag can be provided to the operator.

Sixth Embodiment

A sixth embodiment describes a configuration where the surgical support device 200 has a multiple types of learning models.

Figure 15:
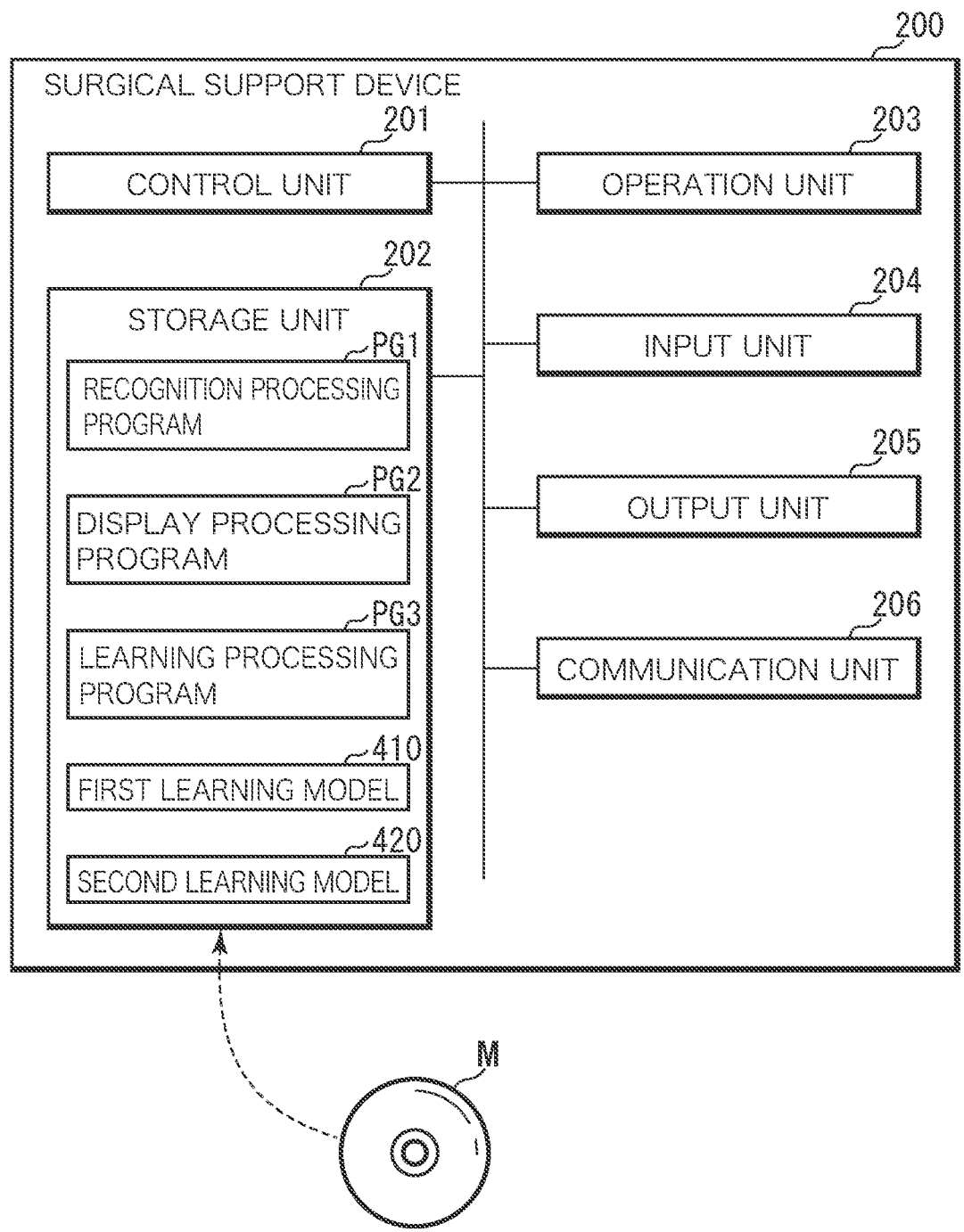
FIG. 15 is a block diagram illustrating the internal configuration of the surgical support device according to a sixth embodiment.

FIG. 15 is a block diagram illustrating the internal configuration of the surgical support device 200 according to the sixth embodiment. The surgical support device 200 according to the sixth embodiment has a first learning model 410 and a second learning model 420. The other configurations of the surgical support device 200 and the overall configuration of the system including the surgical support device 200 are the same as those in the first to fifth embodiments, and thus the description thereof is omitted. Though the present embodiment describes the configuration where the surgical support device 200 has two types of learning models, three or more types of learning models may be provided.

In the sixth embodiment, the first learning model 410 is a learning model used to recognize the loose connective tissue at the range that is closer to the site to be removed (lesion tissue) by endoscopic surgery while the second learning model 420 is a learning model used to recognize the loose connective tissue at the range that is closer to the site to be left (normal tissue) by endoscopic surgery. The loose connective tissue at the range that is closer to the site to be removed (lesion tissue) by endoscopic surgery is also referred to as an outer loose connective tissue, and the loose connective tissue at the range that is closer to the site to be left (normal tissue) by endoscopic surgery is also referred to as an inner loose connective tissue.

The first learning model 410 and the second learning model 420 are similar to the learning model 300 described in the first embodiment, and employ a learning model for image segmentation such as the SegNet and a learning model for object detection such as the YOLO. The first learning model 410 is generated by performing machine learning according to a predetermined algorithm using, as training data, datasets including multiple pairs of the surgical field image and the correct data obtained by selecting, on the pixel-by-pixel basis, the part corresponding to the loose connective tissue closer to the lesion tissue in the surgical field image. Likewise, the second learning model 420 is generated by performing machine learning according to a predetermined algorithm using, as training data, datasets including multiple pairs of the surgical field image and the correct data obtained by selecting, on the pixel-by-pixel basis, the part corresponding to the loose connective tissue closer to the normal tissue in the surgical field image. The configuration of the learning procedure is similar to that of the first embodiment, and thus the description thereof will not be made here.

Figure 16:
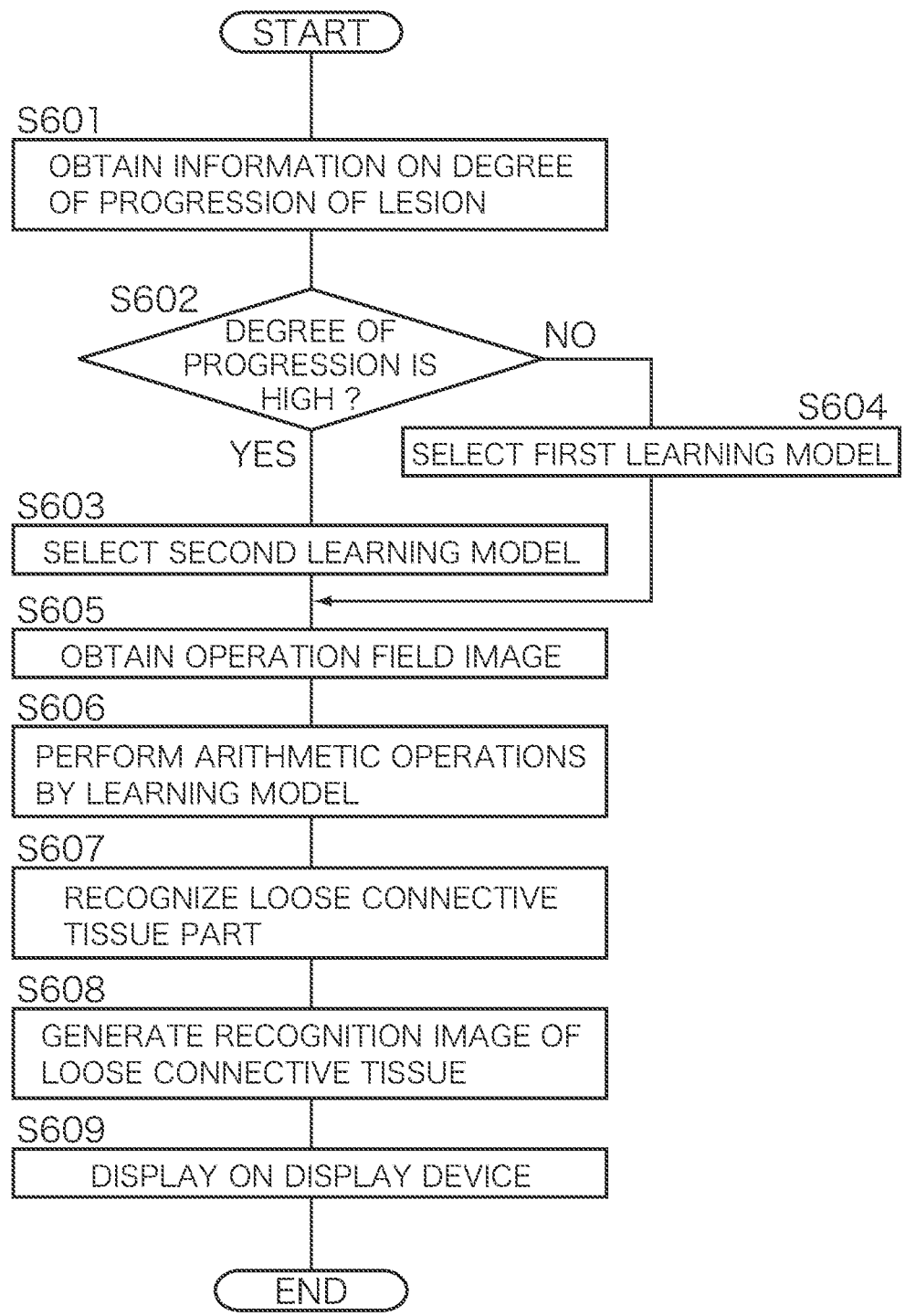
FIG. 16 is a flowchart illustrating the processing procedure to be executed by the surgical support device according to the sixth embodiment.

FIG. 16 is a flowchart illustrating the processing procedure to be executed by the surgical support device 200 according to the sixth embodiment. The control unit 201 of the surgical support device 200 obtains information on the degree of progression of the lesion (step S601). In the case where the degree of progression of the lesion is specified in advance by diagnostic methods such as pre-operative diagnostic imaging and pathological diagnosis, the control unit 201 can accept information on the degree of progression of the lesion through the operation unit 203 or the communication unit 206 before the start of the laparoscopic surgery. Alternatively, the operator who confirms the surgical field image displayed on the display device 130 may determine the degree of progression of the lesion. In this case, the control unit 201 can accept information on the degree of progression of the lesion through the operation unit 203 or the communication unit 206 after the start of the laparoscopic surgery. In addition, having separately prepared a learning model for determining the degree of progression of the lesion, the control unit 201 may determine the degree of progression of the lesion by executing the arithmetic operation using this learning model.

The control unit 201 determines whether or not the degree of progression is high based on the information obtained at step S601 (step S602). For example, the control unit 201 compares the value indicating the degree of progression with the threshold, and determines that the degree of progression is high when the value is equal to or more than the threshold and determines that the degree of progression is low when the value is less than the threshold. The control unit 201 selects the second learning model 420 for gaining a greater margin (step S603) when determining that the degree of progression of the lesion is high (step S602: YES), and selects the first learning model 410 for reducing the range to be resected (step S604) when determining that the degree of progression is low (step S602: NO).

The control unit 201 recognizes the loose connective tissue by using the selected learning model (the first learning model 410 or the second learning model 420) by executing the procedure according to steps S605 to S609 as in the first embodiment and displays on the display device 130 the recognition image of the loose connective tissue superimposed on the surgical field image.

The inner loose connective tissue (closer to the normal tissue) is recognized and displayed on the display device 130 when the degree of progression of the lesion is high, and thus the operator can gain a large margin for the lesion tissue by resecting the inner loose connective tissue displayed on the display device 130. Meanwhile, the outer loose connective tissue (closer to the lesion tissue) is recognized and displayed on the display device 130 when the degree of progression of the lesion is low, and thus, the operator can reduce the range to be resected by resecting the outer loose connective tissue displayed on the display device 130.

Though the sixth embodiment describes the configuration where the control unit 201 selects the first learning model 410 or the second learning model 420 depending on the degree of progression of the lesion, another configuration may be employed where selection of the learning model by the operator himself or herself is accepted. That is, the control unit 201 accepts the selection of the first learning model 410 when the operator wishes to resect the outer loose connective tissue and accepts the selection of the second learning model 420 when the operator wishes to resect the inner loose connective tissue.

The first learning model 410 may be a learning model trained using training data obtained by a first doctor performing annotation, while the second learning model 420 may be a learning model trained using training data obtained by a second doctor performing annotation. The surgical support device 200 may optionally accept the selection of the learning model by the operator through the operation unit 203 or the communication unit 206.

The first learning model 410 and the second learning model 420 may be learning models selected by the patient's attributes. For example, the first learning model 410 may be a learning model selected for patients receiving chemotherapy while the second learning model 420 may be a learning model selected for obese patients. Other learning models may be employed that are selected based on patient's attributes such as age, gender, height and weight. The surgical support device 200 may merely select the learning model (e.g., the first learning model 410, the second learning model 420) based on the patient's attributes with reference to externally entered patient information such as an electronic medical record.

The first learning model 410 and the second learning model 420 may be learning models that are selected depending on the occurrence of bleeding. For example, the first learning model 410 may be a learning model selected when no bleeding occurs while the second learning model 420 may be a learning model selected when bleeding occurs. In this case, the surgical support device 200 may select the first learning model 410 when no bleeding is detected, and may select the second learning model 420 when bleeding is detected. It is noted that a well-known method is used to detect bleeding. For example, the occurrence of bleeding can be determined by detecting the spread of the red area in the surgical field image by image analysis.

The first learning model 410 and the second learning model 420 may be learning models selected depending on the state of the loose connective tissue. For example, the first learning model 410 may be a learning model for recognizing the loose connective tissue covered by adhesion tissue, and the second learning model 420 may be a learning model for recognizing the loose connective tissue not covered by adhesion tissue. The presence or absence of the adhesion tissue is judged by the operator, for example. The surgical support device 200 selects the first learning model 410 when the operator determines that there is an adhesion tissue and enters such information. Meanwhile, the surgical support device 200 selects the second learning model 420 when the operator determines that there is no adhesion tissue and enters such information.

The first learning model 410 and the second learning model 420 may be learning models that are selected depending on the surgical site. For example, the first learning model 410 may be the learning model selected when the surgical site is the stomach, and the second learning model 420 may be the learning model selected when the surgical site is the large intestine. Furthermore, other learning models may be employed that is selected when surgical sites such as inguinal hernia, prostate and lungs are assumed to be the surgical sites. The surgical support device 200 may select a learning model appropriate to the surgical site (e.g., the first learning model 410, the second learning model 420) referring to externally input surgical information such as electronic medical records.

The first learning model 410 and the second learning model 420 may be learning models that are selected depending on the type of the laparoscope 11 and the type of the imaging device 11B. For example, the first learning model 410 may be the learning model selected when the laparoscope 11 manufactured by Company A is used, and the second learning model 420 may be the learning model selected when the laparoscope 11 manufactured by Company B, which is different from Company A, is used. The surgical support device 200 can select either the first learning model 410 or the second learning model 420 based on the device information entered as advance information.

Learning models trained by different algorithms may be employed, such as the first learning model 410 constructed by the SegNet, for example and the second learning model 420 constructed by the U-Net, for example. In this case, the surgical support device 200 may accept the selection of the learning model by the operator through the operation unit 203 or the communication unit 206.

Seventh Embodiment

A seventh embodiment describes the configuration where an optimal learning model is selected depending on the surgical field image to be input.

The surgical support device 200 according to the seventh embodiment includes the first learning model 410 and the second learning model 420 as in the sixth embodiment. The first learning model 410 is a learning model constructed by the SegNet, for example while the second learning model 420 is a learning model constructed by the U-Net, for example. The combination of the neural networks that construct the first learning model 410 and the second learning model 420 is not limited to the combination described above, and any neural network may be employed.

Alternatively, the first learning model 410 and the second learning model 420 may be learning models different in the internal structure. For example, even though constructed using the same neural network, the first learning model 410 and the second learning model 420 may be different in the type of layers, the number of layers, the number of nodes, the connection relationship between nodes or the like.

In addition, the first learning model 410 and the second learning model 420 may be learning models that are trained using different training data. For example, the first learning model 410 may be a learning model trained using training data including correct data annotated by a first expert while the second learning model 420 may be a learning model trained using training data including correct data annotated by a second expert different from the first expert. In addition, the first learning model 410 may be a learning model that is trained using training data including each surgical field image imaged at one medical institution and annotation data (correct data) relative to this surgical field image, and the second learning model 420 is a learning model that may be trained using training data including each surgical field image imaged at another medical institution and annotation data (correct data) relative to this surgical field images.

When receiving an input of surgical field images, the surgical support device 200 performs the arithmetic operation using the first learning model 410 and the arithmetic operation using the second learning model 420 by the control unit 201. In order to perform these arithmetic operations in parallel, the control unit 201 may have multiple arithmetic units (e.g., multiple GPUs). The control unit 201 analyzes the results of the arithmetic operations by the first learning model 410 and the results of the arithmetic operations by the second learning model 420, and selects the learning model (the first learning model 410 or the second learning model 420) suitable for the recognition of loose connective tissue based on the analysis results.

Figure 17A:
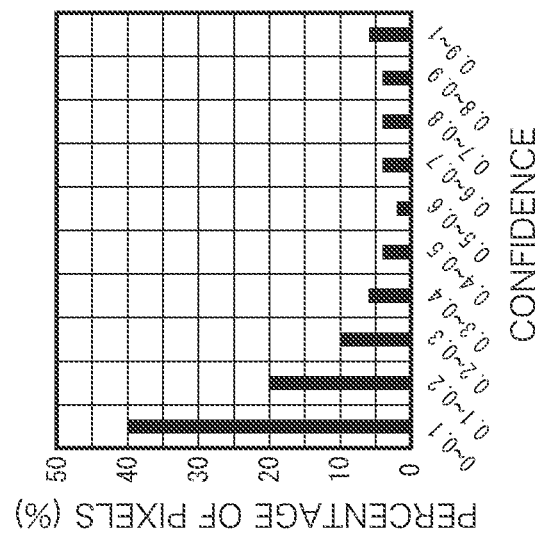
FIGS. 17A-17C illustrate the method of analyzing the results of the arithmetic operation.
Figure 17B:
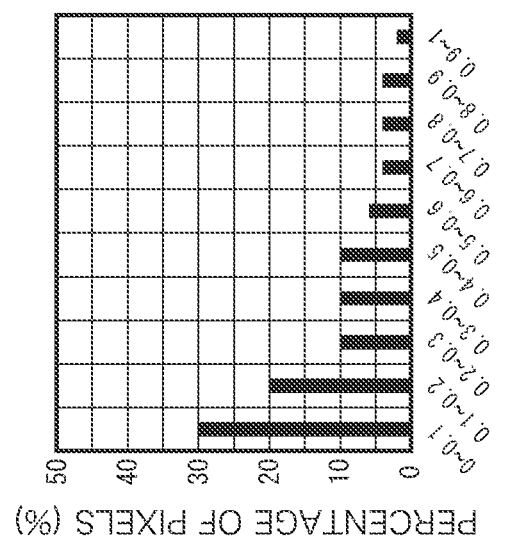
Figure 17C:
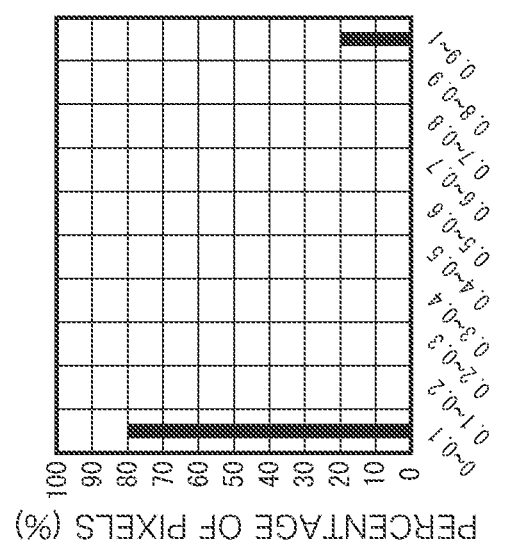

FIGS. 17A-17C illustrate the method of analyzing the results of the arithmetic operations. Each learning model for recognizing the loose connective tissue outputs a probability (confidence) indicating whether or not each pixel corresponds to the loose connective tissue as the result of arithmetic operations. By summing up the number of pixels per confidence, for example, the distributions illustrated in FIGS. 17A-17C can be obtained. As illustrated in FIGS. 17A-17C, the horizontal axis of each graph represents the confidence, and the vertical axis represents the number of pixels (as a percentage of the total image). Ideally, each pixel is classified as having the confidence of 1 (the case where the probability that each pixel is the loose connective tissue is 100%) or the confidence of 0 (the case where the probability that each pixel is the loose connective tissue is 0). Thus, examining the distribution of the confidence based on the results of the arithmetic operations obtained from the ideal learning model yields a bipolar distribution as illustrated in FIG. 17A.

When obtaining the results of the arithmetic operations from the first learning model 410 and the second learning model 420, the control unit 201 of the surgical support device 200 sums up the number of pixels for each confidence and selects the learning model with a distribution close to the ideal distribution. For example, when the distribution obtained from the results of the arithmetic operations by the first learning model 410 is the distribution as illustrated in FIG. 17B, and the distribution obtained from the results of the arithmetic operations by the second learning model 420 is the distribution as illustrated in FIG. 17C, the control unit 201 selects the second learning model 420 since the distribution of the second learning model 420 is closer to the ideal distribution.

The control unit 201 determines whether or not each distribution is close to the ideal distribution by evaluating each distribution using an evaluation factor that increases the evaluation value as the confidence approaches 1 or 0, for example. FIG. 18 illustrates one example of an evaluation factor table. Such an evaluation factor table is prepared in advance in the storage unit 202. In the example in FIG. 18, the evaluation factor is set to take a higher value as the confidence approaches 1 or 0.

When obtaining the results of summing up of the number of pixels per confidence, the control unit 201 calculates a score indicating the quality of the distribution by multiplying each of the results by the evaluation factor. FIGS. 19A-19C illustrate one example of the results of calculating the scores. FIGS. 19A-19C illustrate the results of calculating the scores for the respective distributions illustrated in FIGS. 17A-17C. The score calculated from the ideal distribution is the highest. When the scores are calculated for the distribution evaluated from the results of the arithmetic operations using the first learning model 410, the total score is 84. When the scores are calculated for the distribution evaluated from the results of the arithmetic operations using the second learning model 420, the total score is 188. In this case, the score is higher for the second learning model 420 than the first learning model 410, and thus the control unit 201 selects the second learning model 420 as an appropriate learning model.

Figure 20:
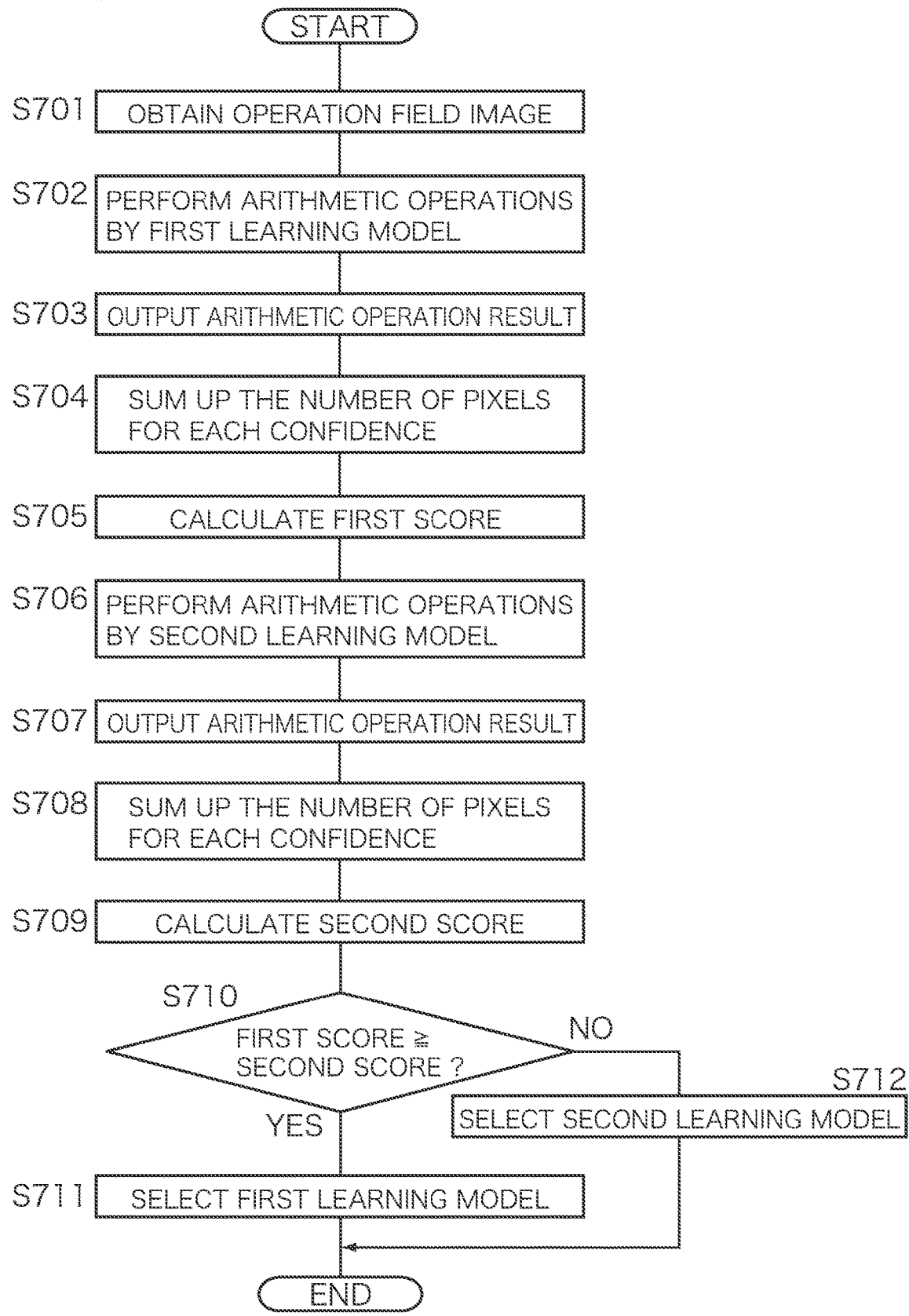
FIG. 20 is a flowchart illustrating the procedure of processing to be executed by the surgical support device according to a seventh embodiment.

FIG. 20 is a flowchart illustrating the procedure of processing to be executed by the surgical support device 200 according to the seventh embodiment. When obtaining the operation field image (step S701), the control unit 201 performs the arithmetic operations by the first learning model 410 (step S702) and obtains the results of the arithmetic operations using the first learning model 410 (step S703). The control unit 201 sums up the number of pixels for each confidence for the first learning model 410 (step S704) and multiplies each of the number of pixels by the evaluation factor to obtain the score (first score) of the distribution (step S705).

Likewise, the control unit 201 performs arithmetic operations using the second learning model 420 on the surgical field image obtained at step S701 (step S706) to obtain the results of the arithmetic operations by the second learning model 420 (step S707). The control unit 201 sums up the number of pixels for each confidence for the second learning model 420 (step S708) and multiplies each of the number of pixels by the evaluation factor to calculate the score (second score) of the distribution (step S709).

Though this flowchart is designed to perform the arithmetic operations for the first learning model 410 (S702-

S705) followed by the arithmetic operation for the second learning model 420 (S706-S709) for the sake of convenience, these arithmetic operations may be performed reversely or may be performed concurrently.

The control unit 201 compares the first score with the second score to determine when the first score is equal to or more than the second score (step S710).

When determining that the first score is equal to or more than the second score (S710: YES), the control unit 201 selects the first learning model 410 as an appropriate learning model (step S711). Hereafter, the control unit 201 performs the recognition processing of the loose connective tissue using the selected first learning model 410.

When determining that the first score is less than the second score (S710: NO), the control unit 201 selects the second learning model 420 as an appropriate learning model (step S712). Hereafter, the control unit 201 performs the processing of recognizing the loose connective tissue using the selected second learning model 420.

As described above, in the seventh embodiment, a more appropriate learning model can be selected for execution of the processing of recognizing the loose connective tissue.

The surgical support device 200 may execute the processing of recognizing the loose connective tissue using the results of the arithmetic operations by the first learning model 410 in the foreground and execute the processing of recognizing loose connective tissue using the results of the arithmetic operations by the second learning model 420 in the background. The control unit 201 evaluates the first learning model 410 and the second learning model 420 at regular intervals, and may switch the learning model used for recognizing the loose connective tissue depending on the evaluation result. Alternatively, the control unit 201 may evaluate the first learning model 410 and the second learning model 420 at the timing instructed by the operator or the like, and may switch the learning model used for recognition of the loose connective tissue according to the evaluation result.

Though the seventh embodiment describes a method using evaluation factors as an evaluation method for the first learning model 410 and the second learning model 420, the evaluation method can employ methods using various statistical indicators, not limited to the method with evaluation factors. For example, the control unit 201 may evaluate the variance and standard deviation in relation to the distribution, and determine that the distribution is bipolar when the variance and standard deviation are high. Moreover, the control unit 201 may take the value of 100–the percentage of pixels (%) on the vertical axis of the graph and evaluate the results of the arithmetic operations for each model by evaluating the kurtosis and skewness of the graph. In addition, the control unit 201 may evaluate the calculation results of each model using the mode, percentile or the like.

Eighth Embodiment

An eighth embodiment describes the configuration where the loose connective tissue and nerves are recognized.

Figure 21:
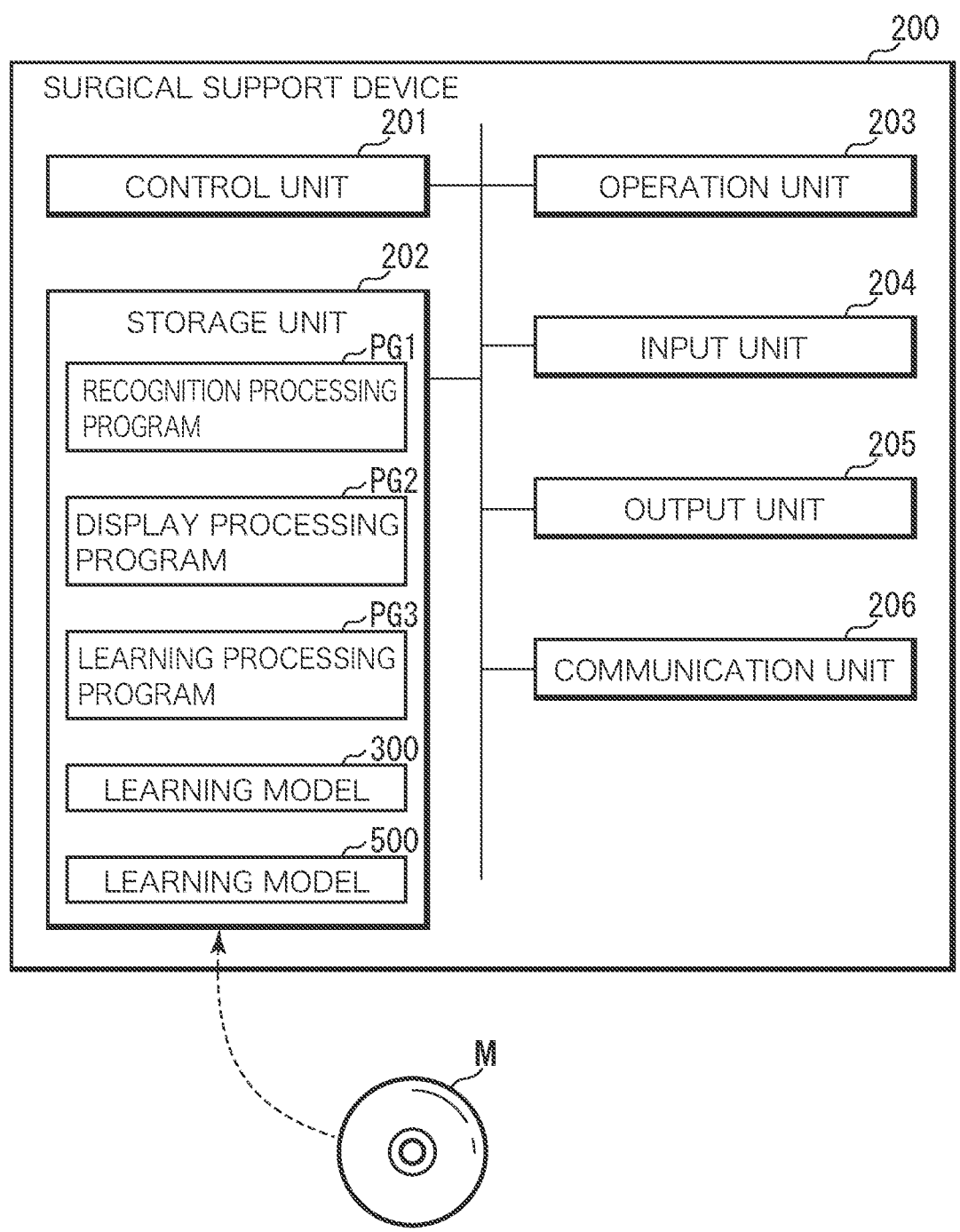
FIG. 21 is a block diagram illustrating the internal configuration of the surgical support device according to an eighth embodiment.

FIG. 21 is a block diagram illustrating the internal configuration of the surgical support device 200 according to the eighth embodiment. The surgical support device 200 according to the eighth embodiment has a learning model 500 for recognizing nerves in addition to the learning model 300 for recognizing the loose connective tissue. Since the rest of the configuration of the surgical support device 200 and the overall configuration of the system including the surgical support device 200 are similar to those in the first to seventh embodiments, the description thereof will not be made here.

As in the learning model 300 described in the first embodiment, the learning model 500 employs a learning model for image segmentation such as the SegNet and a learning model for object detection such as the YOLO, and is so trained as to output information on nerves (e.g., the probability that whether or not each pixel belongs to the nerves) in response to the input of the operation field image.

The learning model 500 is generated by performing machine learning according to a predetermined algorithm using as training data a dataset including multiple pairs of the surgical field images and correct data obtained by selecting, on the pixel-by-pixel basis, the region corresponding to the nerves in the surgical field image. The learning procedure is similar to that of the first embodiment, and thus the description thereof will not be made here.

When acquiring the surgical field image from the input unit 204, the control unit 201 of the surgical support device 200 inputs the acquired surgical field image to the learning model 500 to perform the arithmetic operations using the learning model 500. The control unit 201 recognizes each pixel with a probability of a label output from the softmax layer equal to or more than the threshold (e.g., 50% or more) as a nerve part.

The control unit 201 may recognize the loose connective tissue part by performing the arithmetic operation using the learning model 300 concurrently with the recognition of the nerve part. In addition, the surgical support device 200 may be configured to have multiple arithmetic units (e.g., GPUs) for independently performing the arithmetic operation using the learning model 300 and the arithmetic operation using the learning model 500.

Figure 22:
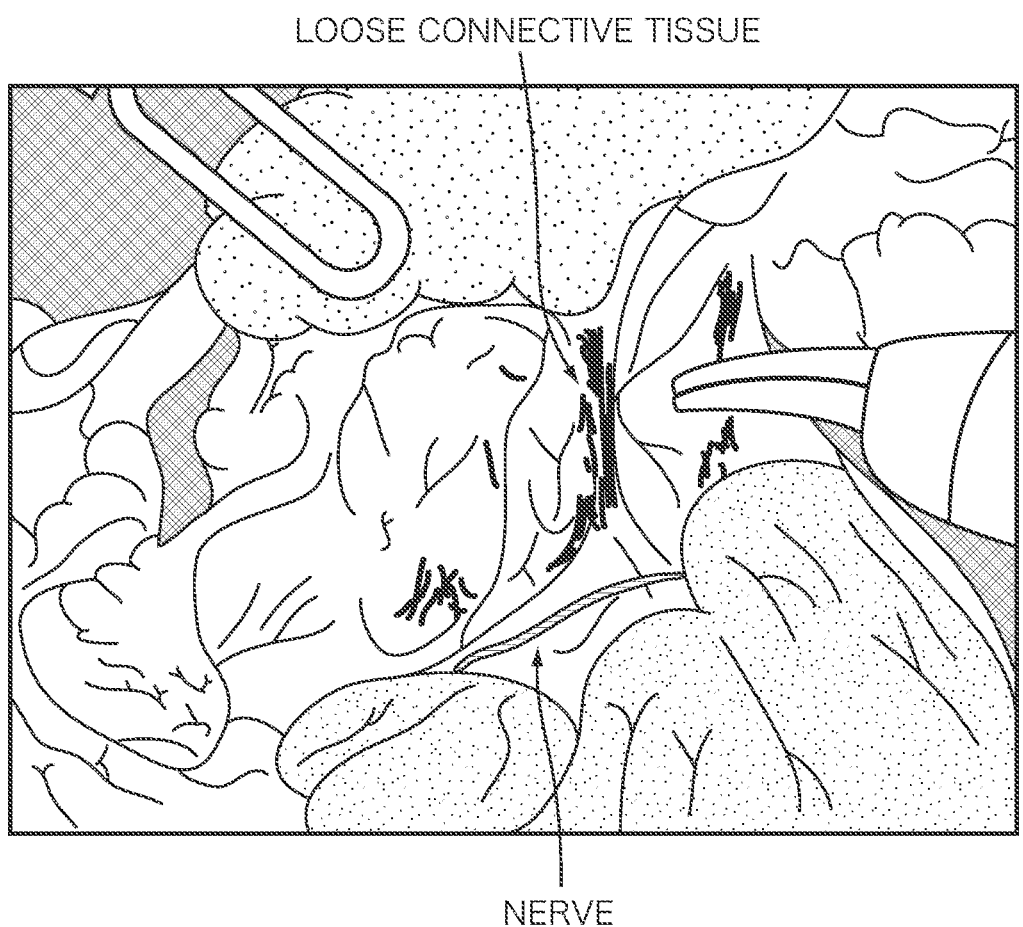
FIG. 22 is a schematic diagram illustrating a display example according to the eighth embodiment.

FIG. 22 is a schematic diagram illustrating a display example according to the eighth embodiment. FIG. 22 displays an example where the recognition result of the loose connective tissue part using the learning model 300 and the recognition result of the nerve part using the learning model 500 are superimposed on the surgical field image. The control unit 201 of the surgical support device 200 generates the recognition image representing the loose connective tissue part and the recognition image representing the nerve part, and displays the two generated recognition images superimposed on the surgical field image to thereby allow the loose connective tissue part and the nerve part. Here, it is more preferable that a specific color (e.g., blue tones) is assigned to the loose connective tissue part, and a different color (e.g., green tones) is assigned to the nerve part. By accepting the selection operation through the operation unit 203, the loose connective tissue part and the nerve part may be displayed so as to arbitrarily be switched.

When the recognition result of the loose connective tissue part using the learning model 300 and the recognition result of the nerve part using the learning model 500 overlap each other, the control unit 201 may select the recognition result with a higher confidence and output information based on the selected recognition result. The confidence of the recognition result using the learning model 300 is calculated based on the probability output from the softmax layer 330. For example, the control unit 201 can calculate the confidence by averaging the probability values for each pixel recognized as the loose connective tissue. The same applies to the confidence of the recognition result using the learning model 500. In the case where a structure in the operation field image is recognized by the learning model 300 as the loose connective tissue with a confidence of 95%, and the same structure is recognized by the learning model 500 as nerves with a confidence of 60%, for example, the control unit 201 may present to the operator the recognition result indicating that the structure is the loose connective tissue.

Figure 23:
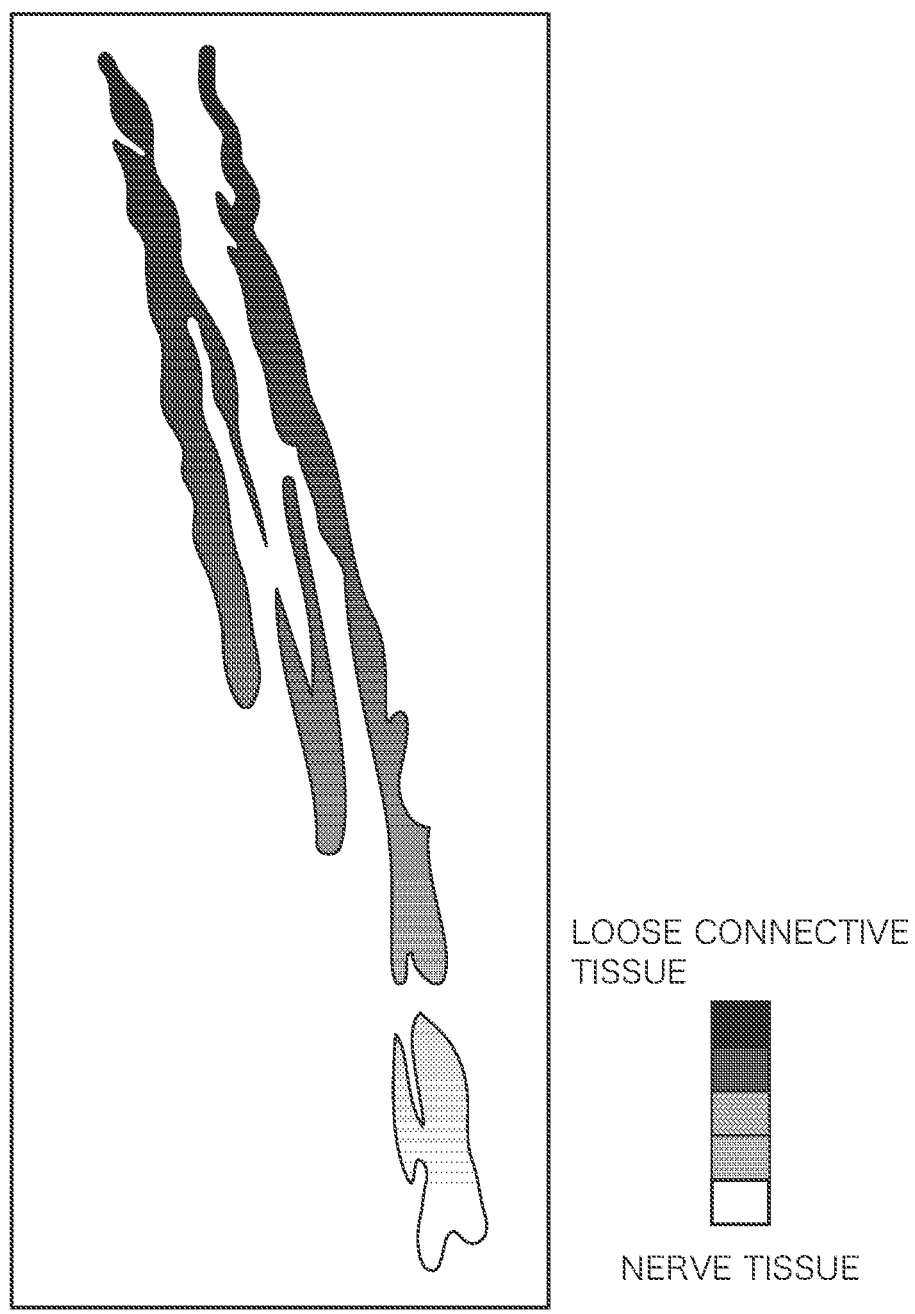
FIG. 23 is a schematic diagram illustrating a display example of the recognition results according to the confidence.

Moreover, when the recognition result of the loose connective tissue part using the learning model 300 and the recognition result of the nerve part using the learning model 500 overlap each other (i.e., when the same pixels are recognized as the loose connective tissue and the nerves), the control unit 201 of the surgical support device 200 may display the recognition results in a display manner depending on the respective confidence. FIG. 23 is a schematic diagram illustrating a display example of the recognition results depending on the confidence. In the example in FIG. 23, the loose connective tissue part and the nerve part are displayed in enlarged dimension. When a structure in the operation field image is recognized as the loose connective tissue with a confidence of 90%, and the same structure is not recognized as the nerve tissue (a confidence of below 50%), for example, the control unit 201 colors the pixels corresponding to the structure with blue tones (black in the drawing) and presents it to the operator. Likewise, when a structure in the operation field image is recognized as the nerve tissue with a confidence of 90%, and the same structure is not recognized as the loose connective tissue (a confidence of below 50%) by the learning model 300, for example, the control unit 201 colors the pixels corresponding to the structure with green tones (white in the drawing) and presents it to the operator. Meanwhile, when a structure in the operation field image is recognized as the loose connective tissue with a confidence of 60%, and the same structure is recognized as the nerve tissue with a confidence of 60%, for example, the control unit 201 colors the structure with an intermediate color between blue tones and green tones (gray in the drawing) and presents it to the operator. The control unit 201 may determine the color applied the pixels corresponding to the structure according to the confidence of the loose connective tissue and the nerves. When the display color of the loose connective tissue part is set to (0, 0, B), and the display color of the nerve tissue part is set to (0, G, 0), for example, the control unit 201 may determine the display color of the pixel having the confidence of X as the loose connective tissue and the confidence of Y as the nerves to be (0, G×Y/(X+Y), B×X/(X+Y)). Though the present embodiment describes the configuration where the display color is changed depending on the confidence, change in the saturation, transparency or the like instead of the display color may be employed.

In the seventh embodiment as described above, it is possible for the surgical support device 200 to recognize the loose connective tissue and the nerves, which are difficult for the operator to discern and to present the recognition results to the operator.

Though the present embodiment describes the configuration where the loose connective tissue and the nerves are recognized, another structure instead of the nerves may be recognized. Here, a structure similar to the loose connective tissue such as lymphatic vessels may be selected for another structure to be recognized along with the loose connective tissue.

Though the present embodiment describes the configuration where display with display colors depending on the confidence may be employed when the recognition results overlap, preferentially displaying the recognition result with a higher confidence may be employed. When a structure included in the operation field image is recognized as the loose connective tissue with a confidence of 95%, and the same structure is recognized as the nerve tissue with a confidence of 60%, for example, the control unit 201 may recognize the structure as the loose connective tissue, and may color it with blue tones and present it to the operator.

Ninth Embodiment

The ninth embodiment describes a user interface provided in the surgical support device 200.

Figure 24:
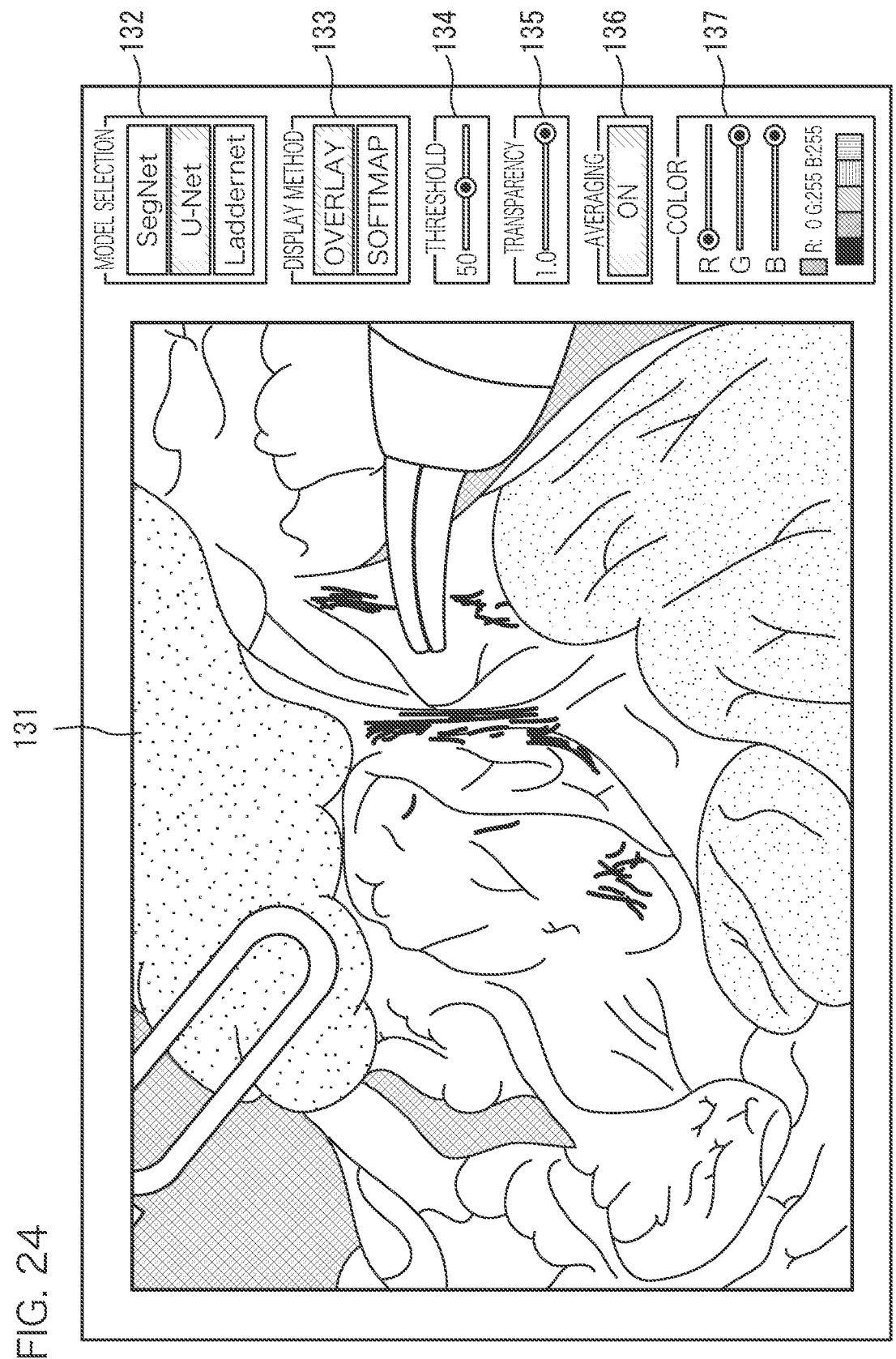
FIG. 24 is a schematic diagram illustrating an example of the configuration of a user interface attached to the surgical support device.

FIG. 24 is a schematic diagram illustrating an example of the configuration of a user interface attached to the surgical support device 200. FIG. 24 illustrates an example in which the display part 131 for displaying the recognition image of the loose connective tissue and the user interface for controlling the display manner of the recognition image are arranged side by side. The user interface illustrated in FIG. 24 is provided with a model selection part 132, a display method selection part 133, a threshold setting part 134, a transparency setting part 135, an averaging instruction part 136 and a display color selection part 137. Various buttons and sliders included in the user interface are operated through the operation unit 203 of the surgical support device 200.

The model selection part 132 has a selection button to select a neural network that constructs the learning model 300. The example in FIG. 24 illustrates a state in which the "U-Net" is being selected. Furthermore, the model selection part 132 may be provided with a selection button to accept the selection of either the first learning model 410 or the second learning model 420 described in the sixth embodiment. Moreover, the model selection part 132 may highlight the recommended model according to the degree of progression of a lesion, the operator in charge of laparoscopic surgery, the condition of the loose connective tissue and the surgical site.

The display method selection part 133 has a selection button to accept either the overlay display or the soft map display. As described in the second embodiment, the overlay display is a display method to uniformly display the loose connective tissue part in a single color while the soft map display is a display method to change the transparency depending on the confidence. FIG. 24 illustrates the state in which the "overlay" display is being selected.

The threshold setting part 134 includes a slider to set the threshold for determining whether or not a pixel of interest is the loose connective tissue. The slider is configured to reduce the threshold (which makes it easier to recognize the loose connective tissue) when slides leftward and is configured to increase the threshold (which makes it harder to recognize the loose connective tissue) when slides rightward.

The transparency setting part 135 has a slider to change the transparency of the loose connective tissue. The slider is configured to lower the transparency when slides leftward and is configured to heighten the transparency when slides rightward.

The averaging instruction part 136 includes an instruction button to turn on or off averaging of the display color. When averaging the display color is turned on, the control unit 201 averages the display color set for the loose connective tissue and the display color of the surgical field image on the background, and displays the loose connective tissue part with the averaged color as a display color. For example, when the display color set for the loose connective tissue part is (0, 0, B1), and the display color set for the loose connective tissue part in the surgical field image of the background (R2, G2, B2), the control unit 201 may display the loose connective tissue part with the color (R2/2, G2/2, (B1+B2)/2). Alternatively, weighting factors W1 and W2 are introduced, and the recognized loose connective tissue part may be displayed with the color (W2×R2, W2×G2, W1×B1+W2×B2).

The display color selection part 137 includes a slider and a color palette to change the display color of the loose connective tissue part. The display color selection part 137 may set the color specified by the slider as the display color of the loose connective tissue part, or may set the color selected by the color palette as the display color of the loose connective tissue part. Furthermore, the display color selection part 137 may also include a default button to return the display color changed by the user to the default display color (e.g., cold colors).

When receiving an instruction of changing the display manner through the model selection part 132, the display method selection part 133, the threshold setting part 134, the transparency setting part 135, the averaging instruction part 136 and the display color selection part 137, the control unit 201 of the surgical support device 200 may change the display manner of the recognition image of the loose connective tissue part displayed on the display part 131 in response to the change instruction.

Though the example in FIG. 24 illustrates the configuration where the model selection part 132, the display method selection part 133, the threshold setting part 134, the transparency setting part 135, the averaging instruction part 136 and the display color selection part 137 are provided, the user interface for controlling the display manner of the recognition image is not limited to those described above. For example, a selection part that accepts capability of inference by the learning model 300 (or the learning model 410, 420, 500) may be provided as a user interface. In addition, a setting part for setting the start time for inference may be provided as a user interface.

In addition, the control unit 201 may accept the change of the display manner through the user interface as illustrated in FIG. 24 and reports the change in the display manner to the operator at an appropriate timing when a change from the default settings occurs. For example, the control unit 201 compares the default setting of the display manner with the current setting of the display manner at the activation of the surgery support device 200 or at the start of the surgery, and when there is a difference between them, may display the difference on the display device 130 or report the difference to the mobile terminal carried by the operator.

It is to be understood that the embodiments disclosed here are illustrative in all respects and not restrictive. The scope of the present invention is defined by the appended claims, not by the above-mentioned meaning, and all changes that fall within the meanings and the bounds of the claims, or equivalence of such meanings and bounds are intended to be embraced by the claims.

It is noted that, as used herein and in the appended claims, the singular forms "a", "an", and "the" include plural referents unless the context clearly dictates otherwise.

The invention claimed is:

1. A computer readable non-transitory recording medium storing a computer program causing a computer to execute processing of:
   acquiring an operation field image obtained by shooting an operation field of an endoscopic surgery; and
   recognizing a loose connective tissue part included in the surgical field image by inputting the surgical field image acquired to a learning model so trained as to output information related to loose connective tissue when the operation field image is input.

2. The computer readable non-transitory recording medium according to claim 1, causing the computer to further execute processing of:
   discernably displaying the loose connective tissue part recognized using the learning model on the surgical field image.

3. The computer readable non-transitory recording medium according to claim 2, causing the computer to execute the processing of:
   displaying the loose connective tissue part colored with a cold color.

4. The computer readable non-transitory recording medium according to claim 2, causing the computer to execute the processing of:
   averaging a display color set to the loose connective tissue part and a display color of the loose connective tissue part in the surgical field image; and
   displaying the loose connective tissue part recognized by being colored with an averaged color.

5. The computer readable non-transitory recording medium according to claim 2, causing the computer to execute the processing of:
   changing a display manner of the loose connective tissue part according to a confidence of a recognition result of the loose connective tissue part.

6. The computer readable non-transitory recording medium according to claim 1, wherein the loose connective tissue is fibrous tissue that binds a site to be removed by the endoscopic surgery and a site to be left by the endoscopic surgery.

7. The computer readable non-transitory recording medium according to claim 1, wherein the loose connective tissue is composed of a plurality of pieces of fibrous tissue, the computer program causing the computer to execute the processing of:
   recognizing a part or all of the plurality of pieces of fibrous tissue as a single cluster based on information output from the learning model.

8. The computer readable non-transitory recording medium according to claim 1, causing the computer to execute the processing of:
   dividing the loose connective tissue part recognized into a plurality of ranges; and
   selectively displaying the loose connective tissue part corresponding to any one of the plurality of ranges divided.

9. The computer readable non-transitory recording medium according to claim 1, wherein the learning model includes a first learning model for recognizing a loose connective tissue part present at a range close to a site to be removed by the endoscopic surgery and a second learning model for recognizing a loose connective tissue part present at a range close to a site to be left by the endoscopic surgery, the computer program causing the computer to execute the processing of:
   selecting the first learning model and the second learning model according to a degree of progression of a lesion part.

10. The computer readable non-transitory recording medium according to claim 1, wherein the learning model includes a first learning model for recognizing a loose connective tissue part present at a range close to a site to be removed by the endoscopic surgery and a second learning model for recognizing a loose connective tissue part present at a range close to a site to be left by the endoscopic surgery, the computer program causing the computer to execute the processing of:

selecting any one of the first learning model and the second learning model depending on an operator.

11. The computer readable non-transitory recording medium according to claim 1, wherein the learning model includes a plurality of types of learning models for recognizing a loose connective tissue part, the computer program causing the computer to execute the processing of:
selecting one learning model out of the plurality of types of the learning models according to an attribute of a patient, a presence or an absence of adhesion tissue that covers the loose connective tissue, a surgical site including the loose connective tissue or a type of an imaging device that images the loose connective tissue.

12. The computer readable non-transitory recording medium according to claim 1, wherein the learning model includes a plurality of types of learning models for recognizing a loose connective tissue part, the computer program causing the computer to execute the processing of:
evaluating each of the learning models based on information output from each of the learning models when the surgical field image is input, and
recognizing a loose connective tissue part included in the surgical field image using any one of the learning models selected based on an evaluation result.

13. The computer readable non-transitory recording medium according to claim 1, wherein the learning model is so trained as to recognize a loose connective tissue part at a stage when the loose connective tissue part with elasticity makes a transition from a state before tension to a state under tension.

14. The computer readable non-transitory recording medium according to claim 1, wherein the learning model is so trained as to recognize a loose connective tissue part in a tense state or a loose connective tissue part such that space exists in a back.

15. The computer readable non-transitory recording medium according to claim 1, wherein the learning model is so trained as to output, along with information on loose connective tissue, information on at least one of two sites connected by the loose connective tissue when an operation field image is input, the computer program causing the computer to execute the processing of:
displaying a recognized site in a manner different from the loose connective tissue part.

16. The computer readable non-transitory recording medium according to claim 1 causing the computer to execute the processing of:
determining whether or not a specific site within the surgical field is stationary; and
switching between display and non-display of the loose connective tissue part according to a determination result.

17. The computer readable non-transitory recording medium according to claim 1 causing the computer to execute the processing of:
determining whether or not a surgical tool included in the surgical field is stationary; and
switching between display and non-display of the loose connective tissue part according to a determination result.

18. The computer readable non-transitory recording medium according to claim 1 causing the computer to execute the processing of:
inputting the surgical field image acquired to a learning model so trained as to output information on a structure different from loose connective tissue when the operation field image is input and recognizing a structure part included in the surgical field image; and
displaying a recognition result in a display manner according to a confidence of recognition of the loose connective tissue part and a confidence of recognition of the structure part.

19. A method for generating a learning model using a computer, comprising:
acquiring training data including an operation field image obtained by shooting an operation field of endoscopic surgery and correct data indicating a loose connective tissue part within the surgical field image; and
generating a learning model that outputs information on loose connective tissue based on sets of training data acquired when the operation field image is input.

20. The method for generating a learning model according to claim 19, wherein
the correct data is data obtained by attaching a correct label to a part having elasticity, a part having a space at a back or a fibrous part kept under tension, out of the loose connective tissue appearing in the surgical field image.

21. A surgical support device, comprising:
a processor; and
a storage storing instructions causing the processor to execute processes of:
acquiring an operation field image obtained by shooting an operation field of endoscopic surgery;
recognizing a loose connective tissue part included in the surgical field image acquired using a learning model so trained as to output information related to loose connective tissue when the operation field image is input; and
outputting support information related to the endoscopic surgery based on a recognition result.

22. An information processing method using a computer, comprising:
acquiring an operation field image obtained by shooting an operation field of endoscopic surgery;
recognizing a loose connective tissue part included in the surgical field image acquired using a learning model so trained as to output information related to loose connective tissue when the operation field image is input; and
outputting support information related to the endoscopic surgery based on a recognition result.

* * * * *